US010188688B2

(12) United States Patent
Lazdunski et al.

(10) Patent No.: US 10,188,688 B2
(45) Date of Patent: Jan. 29, 2019

(54) THERAPY FOR PROMOTING CELL GROWTH

(71) Applicant: MOLEAC PTE. LTD., Singapore (SG)

(72) Inventors: Michel Maurice Jacques Lazdunski, Nice (FR); Catherine Louise Heurteaux, Antibes (FR); David Picard, Singapore (SG)

(73) Assignee: MOLEAC PTE. LTD., Singapore (SG)

( * ) Notice: Subject to any disclaimer, the term of this patent is extended or adjusted under 35 U.S.C. 154(b) by 447 days.

(21) Appl. No.: 15/018,505

(22) Filed: Feb. 8, 2016

(65) Prior Publication Data
US 2016/0235795 A1    Aug. 18, 2016

Related U.S. Application Data

(63) Continuation of application No. 13/260,038, filed as application No. PCT/SG2010/000122 on Mar. 29, 2010, now Pat. No. 9,289,459.

(60) Provisional application No. 61/164,352, filed on Mar. 27, 2009.

(51) Int. Cl.
| | |
|---|---|
| *A61K 36/232* | (2006.01) |
| *A61K 36/69* | (2006.01) |
| *A61K 36/236* | (2006.01) |
| *A61K 36/481* | (2006.01) |
| *A61K 36/537* | (2006.01) |
| *A61K 36/736* | (2006.01) |
| *A61K 36/882* | (2006.01) |
| *A61K 45/06* | (2006.01) |
| *A61K 35/62* | (2006.01) |
| *A61K 36/286* | (2006.01) |
| *A61K 36/65* | (2006.01) |
| *A61K 38/00* | (2006.01) |

(52) U.S. Cl.
CPC ............ *A61K 36/232* (2013.01); *A61K 35/62* (2013.01); *A61K 36/236* (2013.01); *A61K 36/286* (2013.01); *A61K 36/481* (2013.01); *A61K 36/537* (2013.01); *A61K 36/65* (2013.01); *A61K 36/69* (2013.01); *A61K 36/736* (2013.01); *A61K 36/882* (2013.01); *A61K 45/06* (2013.01); *A61K 38/00* (2013.01)

(58) Field of Classification Search
CPC .... A61K 36/232; A61K 36/69; A61K 36/236; A61K 36/481
USPC ......................................................... 424/725
See application file for complete search history.

(56) References Cited

U.S. PATENT DOCUMENTS

| | | | |
|---|---|---|---|
| 4,469,685 A * | 9/1984 | Kojima ................. | A61K 36/00 424/728 |
| 6,447,814 B1 | 9/2002 | Lee et al. | |
| 6,746,695 B1 * | 6/2004 | Martin ................. | A61K 36/185 210/656 |
| 7,205,004 B2 | 4/2007 | Xia | |
| 7,410,657 B2 * | 8/2008 | Lee ........................ | A61K 36/00 424/725 |
| 2002/0009506 A1 * | 1/2002 | Tao ....................... | A61K 31/355 424/728 |
| 2002/0031559 A1 * | 3/2002 | Liang ..................... | A61K 9/02 424/725 |
| 2003/0211178 A1 | 11/2003 | Xia | |
| 2004/0191344 A1 * | 9/2004 | Wang ................... | A61K 31/593 424/776 |
| 2005/0233377 A1 | 10/2005 | Zhang et al. | |
| 2007/0059386 A1 * | 3/2007 | Lee ........................ | A61K 36/00 424/725 |
| 2007/0178178 A1 | 8/2007 | Xia | |
| 2009/0004300 A1 * | 1/2009 | Lee ........................ | A61K 36/00 424/728 |
| 2009/0162459 A1 | 6/2009 | Shi et al. | |

FOREIGN PATENT DOCUMENTS

| | | |
|---|---|---|
| CN | 1144097 A | 3/1997 |
| CN | 1418645 A | 5/2003 |
| CN | 1686299 A | 10/2005 |
| CN | 101099836 A | 1/2008 |
| CN | 101244239 A | 8/2008 |
| CN | 101279016 A | 10/2008 |
| CN | 101361923 A | 2/2009 |
| CN | 101390423 A | 3/2009 |
| CN | 102091166 A | 6/2011 |
| EP | 2095826 A1 | 9/2009 |
| RU | 2330675 C2 | 8/2008 |
| RU | 2341270 C2 | 12/2008 |
| WO | WO-2006/008582 A1 | 1/2006 |
| WO | WO-2007/043796 A1 | 4/2007 |
| WO | WO-2007/106049 A1 | 9/2007 |

(Continued)

OTHER PUBLICATIONS

Abu Ali Ibn-e-Sina, Al-Qaanoon-fil-Tibb, vol. II (11th century AD), Institute of History of Medicine and Medical Research, Jamia Hamdard, New Delhi-62, p. 169 (1987). Formulation ID: AH1/259, Fomrulation Name: Khokh/Shartaloo—Exhibit 2 (Translation).

Abu Bakr Mohammad Bin Zakariyya Al-Razi, Kitaab-al-Haawi-fil-Tibb, vol. I (9th century AD), Dayerah-al-Ma'aarif Usmania, Hyderabad, p. 71 (1974). Formulation ID: AA1/143, Formlation Name: Ghiza-e-Dawaee Barae Rasha—Exhibit 3 (Translation).

Abu Bakr Mohammad Bin Zakariyya Al-Razi, Kitaab-al-Haawi-fil-Tibb, vol. I (9th century AD), Dayerah-al-Ma'aarif Usmania, Hyderabad, p. 75 (1974). Formulation ID: AA1/170, Formlation Name: Shorba Bara-e-Raasha (Translation).

(Continued)

*Primary Examiner* — Christopher R Tate
(74) *Attorney, Agent, or Firm* — Marshall, Gerstein & Borun LLP

(57) ABSTRACT

There is disclosed the use of a composition for promoting neuronal growth of neurons in tissues of the central or peripheral nervous system. There is also disclosed a method for inducing proliferation or differentiation of neuronal cells.

6 Claims, 11 Drawing Sheets

(56) References Cited

FOREIGN PATENT DOCUMENTS

WO  WO 2008/059959 A1  5/2008
WO  WO-2010/053456 A1  5/2010

OTHER PUBLICATIONS

Chinese Medicine Neuroaid Efficacy on Stroke Recovery, Clinical Trial ID: NCT00554723 <http://clinicaltrials.gov/archive/NCT00554723/2009_01_21>, last updated Jan. 21, 2009.

Ding-Zhou et al., "L-NAME Reduces Infarction, Neurological Deficit and Blood-Brain Barrier Disruption Following Cerebral Ischemia in Mice," *Eur. J. Pharmacol.*, 457:137-146 (2002).

Gao et al., "Verification of the Formulation and Efficacy of *Danggui Buxue Tang* (a Decoction of *Radix Astragali* and *Radix Angelicae Sinensis*): an Exemplifying Systematic Approach to Revealing the Complexity of Chinese Herbal Medicine Formulae," *Chinese Medicine*, 2(12):1-10 (2007).

Golanov et al., "Contribution and Cerebral Edema to the Neuronal Salvage Elicited by Stimulation of Cerebellar Fastigial Nucleus after Occlusion of the Middle Cerebral Artery in Rat," *J. Cereb. Blood Flow Metab.*, 15:172-173 (1995).

Heurteaux et al., "Deletion of the Background Potassim Channel TREK-1 Results in a Depression-Resistant Phenotype," *Nat. Neurosci.*, 9:1134-1141 (2006).

Huang et al., "Effects of Cerebral Ischemia in Mice Deficient in Neuronal Nitric Oxide Synthase," *Science*, 265:1883-1885 (1994).

International Preliminary Report on Patentability for Application No. PCT/SG2010/000122, dated Jun. 10, 2011.

International Search Report and Written Opnion for Application No. PCT/SG2010/000122, dated Jun. 10, 2010.

Koh et al., "Vulnerability of Cultured Cortical Neurons to Damage by Excitotoxins: Differential Susceptibility of Neurons Containing NADPH-Diaphorase," *J. Neurosci.*, 8(6):2153-2163 (1988).

Mahendra Bhaugike, Dhanvantarinighantauh—Edited by P.V. Sharma, Translated by Guru Prasad Sharma, Chaukhambha Orientalia, Varanasi, 3rd Edition, p. 154 (2002). Formulation ID: AK12/372; Formulation Name: Aarukam—Exhibit 1 (Translation).

Meng et al., "Angiogenic Effects of the Extracts from Herbs: Angelica and Chuanxiong," *Am. J. Chin. Med.*, 36(3):541-554 (2008).

Mohammad Shareef Khan, Ilaaj-al-Amraaz (18th century AD), Afzal-al-Matabe, Barqi Press, Delhi, p. 287 (1921). Formulation ID: MH1/3382, Formulation Name: Majoon-e-Sanjari—Exhibit 5 (Translation).

Official Action issued in connection with Russian Patent Application No. 2011139190/15(058527), dated Sep. 29, 2014.

Pool et al., "NeuriteTracer: A Novel Image J Plugin for Automated Quantification of Neurite Outgrowth," *J. Neurosci. Methods*, 168(1):134-139 (2008).

Siow, "Neuroaid in Stroke Recovery," *Euro. Neurol.*, 60:264-266 (2008).

\* cited by examiner

Epifluorescence Microscopy

Control        NeuroAid 1µg/ml

DAY 3

DAY 14

*Confocal Microscopy*

Day 14
NeuroAid 1µg/ml

THERAPY FOR PROMOTING CELL GROWTH

TECHNICAL FIELD

The present invention generally relates to methods and compositions for promoting neuronal outgrowth and proliferation. The present invention also relates to an in vitro method for promoting cell growth.

BACKGROUND

Nervous system injuries affect numerous people every year. As a result of this high incidence of neurological injuries, nerve regeneration and repair is becoming a rapidly growing field dedicated to the discovery of new ways to recover nerve functionality after injury. However up to now, clinically repairing central nervous system (CNS) lesions and recovering neurological functions for patients suffering from nervous system injuries have been problematic. Thus, patients with various forms of nervous system diseases, such as amyotrophic lateral sclerosis (ALS) and senile dementia, have always been told by their physicians that it would be difficult to recover their neurological functions.

The ability of neurons to extend neurites (such as axons and dendrites) is of prime importance in establishing neuronal connections during development. It is also required during neuroregeneration to re-establish connections destroyed as a result of a lesion. However, axons in the central nervous system have a very limited capacity to re-grow after a lesion. Thus, for diseases such as senile dementia, in which there is a progressive degeneration of neuronal cells, the research of therapeutic agents or molecules which are able to stimulate neuronal cell outgrowth and proliferation, will open a new therapeutic strategy which focuses on neural repair and restoring neurological function.

There is a need to improve methods of treating nervous system injuries and neurological diseases. More specifically, there is a need to provide regenerative therapies which can promote neuronal outgrowth and proliferation of neurons so as to enable damaged or diseases nerves to function again.

SUMMARY

According to a first aspect, there is provided the use of a composition comprising at least two components selected from the group consisting of the following: Radix et Rhizoma Salviae Miltiorrhizae (Red Sage root or Dan Shen), *Prunus Persica* (Peach seed or Taoren), Radix Polygalae (root of thinleaf milkwort, *Polygala tenuifolia* Willd., *Polygala sibirica* L. or Yuanzhi) and Rhizoma acori Tatarinowii (rhizome of grassleaf sweetflag or Shichangpu) and combinations thereof, and an optional component selected from the group consisting of: Radix Astragali (root of Membranous Milkvetch or Huang Qi), Radix Paeoniae Rubra (Red Peony root, *Paeonia lactiflora* Pall, *Paeonia veitchii* Lynch or Chi Shao), rhizome of *Ligusticum Chuanxiong* (Chuan Xiong), Flower of *Carthamus Tinctorius* (Safflower or HongHua), and radix angelicae *sinensis* (root of Chinese Angelica or DanGui) and combinations thereof, in the manufacture of a medicament for promoting neuronal outgrowth and proliferation of neurons in tissues of the central or peripheral nervous system.

In one embodiment, the composition of the first aspect further comprises an optional component selected from the group consisting of: *Buthus martensii* (dried body of scorpio or Quanxie), *Eupolyphaga* Seu Seteleophaga (dried body of ground beetle, *Eupolyphaga sinensis* Walker, *Steleophaga plancyi* or Tubiechong), *Calculus Bovis* Artifactus (Natural or Artificial cow-bezoar or Rengong Niuhuang), Cornu Saigae Tataricae (Antelope Horn or Lingyangjiao) and dried body of leeches (*Hirudo, Whitmania pigra* Whitman, *Hirudo nipponica* Whitman *Whitmania acranulata* Whitman or Shuizhi).

Advantageously, the medicament can induce neuronal outgrowth of neurons and proliferation in diseased or injured tissue where significant tissue shrinkage, loss, atrophy or cell death has occurred. Promoting neuronal outgrowth and proliferation of neurons enable damaged or disease nerve to perform directional outward growth that may introduce beneficial synapse connection or be replaced with new functioning cells. The composition may also promote stem cell differentiation and recruitment into the diseased or injured tissue.

In one embodiment, there is provided the use of a composition comprising a first component selected from the group consisting of the following components: Radix et Rhizoma Salviae Miltiorrhizae (Red Sage root or Dan Shen), *Prunus Persica* (Peach seed or Taoren), Radix Polygalae (root of thinleaf milkwort, *Polygala tenuifolia* Willd., *Polygala sibirica* L. or Yuanzhi), *Buthus martensii* (dried body of scorpio or Quanxie), Rhizoma acori Tatarinowii (rhizome of grassleaf sweetflag or Shichangpu), *Eupolyphaga* Seu Seteleophaga (dried body of ground beetle, *Eupolyphaga sinensis* Walker, *Steleophaga plancyi* or Tubiechong), *Calculus Bovis* Artifactus (Natural or Artificial cow-bezoar or Rengong Niuhuang), and Cornu Saigae Tataricae (Antelope Horn or Lingyangjiao) and combinations thereof, and an optional second component selected from the group consisting of: Radix Astragali (root of Membranous Milkvetch or Huang Qi), Radix Paeoniae Rubra (Red Peony root, *Paeonia lactiflora* Pall, *Paeonia veitchii* Lynch or Chi Shao), rhizome of *Ligusticum Chuanxiong* (Chuan Xiong), Flower of *Carthamus Tinctorius* (Safflower or HongHua), radix angelicae sinensis (root of Chinese Angelica or DanGui) and dried body of leeches (*Hirudo, Whitmania pigra* Whitman, *Hirudo nipponica* Whitman *Whitmania acranulata* Whitman or Shuizhi) and combinations thereof, in the manufacture of a medicament for treating patients having a condition selected from the group of depression, psychiatric indications, natural aging and traumatic brain cell death, for diminishing the effects of stroke or neurodegeneration in predisposed subjects or subjects at risk of stroke or neurodegeneration, for treating a patient having a diseased or injured tissues of the central and peripheral nervous system and for promoting cell growth.

According to a second aspect, there is provided the use of a composition comprising at least two of the following components: Radix Astragali (root of Membranous Milkvetch or Huang Qi), Radix et Rhizoma Salviae Miltiorrhizae (Red Sage root or Dan Shen), Radix Paeoniae Rubra (Red Peony root, *Paeonia lactiflora* Pall, *Paeonia veitchii* Lynch or Chi Shao), rhizome of *Ligusticum Chuanxiong* (Chuan Xiong), radix angelicae sinensis (root of Chinese Angelica or DanGui), Flower of *Carthamus Tinctorius* (Safflower or HongHua), *Prunus Persica* (Peach seed or Taoren), Radix Polygalae (root of thinleaf milkwort, *Polygala tenuifolia* Willd., *Polygala sibirica* L. or Yuanzhi) and Rhizoma acori Tatarinowii (rhizome of grassleaf sweetflag or Shichangpu) in the manufacture of a medicament for treating patients having a condition selected from the group of depression, psychiatric indications, natural aging and traumatic brain cell death.

Whilst not bound by theory, we believe that the medicament as disclosed herein may be useful for treating patients with depression or other psychiatric indications such as schizophrenia and anxiety disorders by promoting the regulation of hormonal balance that may have been disrupted by loss of cell function.

According to a third aspect, there is provided the use of a composition comprising at least three of the following components: Radix Astragali (root of Membranous Milkvetch or Huang Qi), Radix et Rhizoma Salviae Miltiorrhizae (Red Sage root or Dan Shen), Radix Paeoniae Rubra (Red Peony root, *Paeonia lactiflora* Pall, *Paeonia veitchii* Lynch or Chi Shao), rhizome of *Ligusticum Chuanxiong* (Chuan Xiong), radix *angelicae sinensis* (root of Chinese Angelica or DanGui), Flower of *Carthamus Tinctorius* (Safflower or HongHua), *Prunus Persica* (Peach seed or Taoren), Radix Polygalae (root of thinleaf milkwort, *Polygala tenuifolia* Willd., *Polygala sibirica* L. or Yuanzhi) and Rhizoma acori Tatarinowii (rhizome of grassleaf sweetflag or Shichangpu) in the manufacture of a medicament for diminishing the effects of stroke or neurodegeneration in predisposed subjects or subjects at risk of stroke or neurodegeneration.

According to a fourth aspect, there is provided the use of a composition comprising at least three of the following components: Radix Astragali (root of Membranous Milkvetch or Huang Qi), Radix et Rhizoma Salviae Miltiorrhizae (Red Sage root or Dan Shen), Radix Paeoniae Rubra (Red Peony root, *Paeonia lactiflora* Pall, *Paeonia veitchii* Lynch or Chi Shao), rhizome of *Ligusticum Chuanxiong* (Chuan Xiong), radix *angelicae sinensis* (root of Chinese Angelica or DanGui), Flower of *Carthamus Tinctorius* (Safflower or HongHua), *Prunus Persica* (Peach seed or Taoren), Radix Polygalae (root of thinleaf milkwort, *Polygala tenuifolia* Willd., *Polygala sibirica* L. or Yuanzhi) and Rhizoma acori Tatarinowii (rhizome of grassleaf sweetflag or Shichangpu) in the manufacture of a medicament for promoting cell growth.

In one embodiment, the medicament may promote controlled growth of chondrocytes, skeletal muscle cells, myocardiums, smooth muscle cells, hepatocytes, kidney cells and epithelial skin cells. A medicament that promotes cell growth may be used for treating conditions such as rheumatoid arthritis, muscle degenerative disorders, stroke, kidney and liver diseases. The medicament may also be used for delaying aging processes by improving epithelial or epidermal cell proliferations or functions.

According to a fifth aspect, there is provided the use of at least one of the following components: Radix Astragali (root of Membranous Milkvetch or Huang Qi), Radix et Rhizoma Salviae Miltiorrhizae (Red Sage root or Dan Shen), Radix Paeoniae Rubra (Red Peony root, *Paeonia lactiflora* Pall, *Paeonia veitchii* Lynch or Chi Shao), rhizome of *Ligusticum Chuanxiong* (Chuan Xiong), radix *angelicae sinensis* (root of Chinese Angelica or DanGui), Flower of *Carthamus Tinctorius* (Safflower or HongHua), *Prunus Persica* (Peach seed or Taoren), Radix Polygalae (root of thinleaf milkwort, *Polygala tenuifolia* Willd., *Polygala sibirica* L. or Yuanzhi) and Rhizoma acori Tatarinowii (rhizome of grassleaf sweetflag or Shichangpu) in the manufacture of a medicament, and a supplemental agent, for treating a patient having a diseased or injured tissues of the central or peripheral nervous system.

In one embodiment, there is provided the use of the composition as defined above, wherein the composition comprises at least 2, 3, 4, 5, 6, 7, 8, 9, 10, 11, 12, 13 or 14, of the components. The supplemental agent may be mineral supplements, vitamins, herbal supplements, Western Medicine or fish oils.

According to a sixth aspect, there is provided a cell culture reagent for promoting cell survival and growth comprising a culture medium and at least one of the following components: Radix Astragali (root of Membranous Milkvetch or Huang Qi), Radix et Rhizoma Salviae Miltiorrhizae (Red Sage root or Dan Shen), Radix Paeoniae Rubra (Red Peony root, *Paeonia lactiflora* Pall, *Paeonia veitchii* Lynch or Chi Shao), rhizome of *Ligusticum Chuanxiong* (Chuan Xiong), radix *angelicae sinensis* (root of Chinese Angelica or DanGui), Flower of *Carthamus Tinctorius* (Safflower or HongHua), *Prunus Persica* (Peach seed or Taoren), Radix Polygalae (root of thinleaf milkwort, *Polygala tenuifolia* Willd., *Polygala sibirica* L. or Yuanzhi) and Rhizoma acori Tatarinowii (rhizome of grassleaf sweetflag or Shichangpu).

In one embodiment, there is provided a cell culture reagent comprising the composition as defined in the sixth aspect, wherein the composition comprises at least 2, 3, 4, 5, 6, 7, 8, 9, 10, 11, 12, 13 or 14 of the components.

In another embodiment, the cell culture reagent may promote cell survival and growth of neurons, stem cells, chondrocytes, skeletal muscle cells, myocardiums, smooth muscle cells, hepatocytes, kidney cells, islets of langerhans and epithelial skin cells.

According to a seventh aspect, there is provided a method for promoting cell survival, inducing proliferation or differentiation of cells, comprising contacting said cells with an effective amount of at least three of the following components: Radix Astragali (root of Membranous Milkvetch or Huang Qi), Radix et Rhizoma Salviae Miltiorrhizae (Red Sage root or Dan Shen), Radix Paeoniae Rubra (Red Peony root, *Paeonia lactiflora* Pall, *Paeonia veitchii* Lynch or Chi Shao), rhizome of *Ligusticum Chuanxiong* (Chuan Xiong), radix *angelicae sinensis* (root of Chinese Angelica or DanGui), Flower of *Carthamus Tinctorius* (Safflower or HongHua), *Prunus Persica* (Peach seed or Taoren), Radix Polygalae (root of thinleaf milkwort, *Polygala tenuifolia* Willd., *Polygala sibirica* L. or Yuanzhi) and Rhizoma acori Tatarinowii (rhizome of grassleaf sweetflag or Shichangpu).

The contacting step of the seventh aspect may be undertaken in vitro. An in vitro contacting step may promote cell growth, differentiation or cell survival would facilitate in vitro culture of various cells that may be used for tissue engineering or ex vivo therapeutic uses. In one embodiment, the effective amount is 1 g to 8 g. In another embodiment, the neuronal cells are vertebrate neuronal cells, preferably human neuronal cells. In one embodiment, the neuronal cells are derived from cortical neuronal cells.

According to an eight aspect, there is provided a method of promoting neuronal outgrowth and proliferation of neurons in tissues of the central or peripheral nervous system of a patient comprising the step of administering to said patient a composition comprising at least two components selected from the group consisting of the following: Radix et Rhizoma Salviae Miltiorrhizae (Red Sage root or Dan Shen), *Prunus Persica* (Peach seed or Taoren), Radix Polygalae (root of thinleaf milkwort, *Polygala tenuifolia* Willd., *Polygala sibirica* L. or Yuanzhi) and Rhizoma acori Tatarinowii (rhizome of grassleaf sweetflag or Shichangpu) and combinations thereof.

According to a ninth aspect, there is provided a method of treating patients having a condition selected from the group of depression, psychiatric indications, natural aging and traumatic brain cell death comprising the step of administering to said patients at least two of the following components: Radix Astragali (root of Membranous Milkvetch or Huang Qi), Radix et Rhizoma Salviae Miltiorrhizae (Red Sage root or Dan Shen), Radix Paeoniae Rubra (Red Peony root, *Paeonia lactiflora* Pall, *Paeonia veitchii* Lynch or Chi Shao), rhizome of *Ligusticum Chuanxiong* (Chuan Xiong), radix *angelicae sinensis* (root of Chinese Angelica or DanGui), Flower of *Carthamus Tinctorius* (Safflower or HongHua), *Prunus Persica* (Peach seed or Taoren), Radix Polygalae (root of thinleaf milkwort, *Polygala tenuifolia* Willd., *Polygala sibirica* L. or Yuanzhi) and Rhizoma acori Tatarinowii (rhizome of grassleaf sweetflag or Shichangpu).

According to a tenth aspect, there is provided a method for diminishing the effects of stroke or neurodegeneration in predisposed subjects or subjects at risk of stroke or neurodegeneration comprising the step of administering to said subjects at least three of the following components: Radix Astragali (root of Membranous Milkvetch or Huang Qi), Radix et Rhizoma Salviae Miltiorrhizae (Red Sage root or Dan Shen), Radix Paeoniae Rubra (Red Peony root, *Paeonia lactiflora* Pall, *Paeonia veitchii* Lynch or Chi Shao), rhizome of *Ligusticum Chuanxiong* (Chuan Xiong), radix *angelicae sinensis* (root of Chinese Angelica or DanGui), Flower of *Carthamus Tinctorius* (Safflower or HongHua), *Prunus Persica* (Peach seed or Taoren), Radix Polygalae (root of thinleaf milkwort, *Polygala tenuifolia* Willd., *Polygala sibirica* L. or Yuanzhi) and Rhizoma acori Tatarinowii (rhizome of grassleaf sweetflag or Shichangpu).

Glossary of Terms

This section is intended to provide guidance on the interpretation of the words and phrases set forth below (and where appropriate grammatical variants thereof).

The term "neuronal outgrowth" in the specification relates to the general directional outward growth of axons and dendrites. Neuronal outgrowth is important in synapse formation or development.

Unless specified otherwise, the terms "comprising" and "comprise", and grammatical variants thereof, are intended to represent "open" or "inclusive" language such that they include recited elements but also permit inclusion of additional, unrecited elements.

As used herein, the term "about" as used in relation to a numerical value means, for example, +50% or +30% of the numerical value, preferably +20%, more preferably +10%, more preferably still +5%, and most preferably +1%. Where necessary, the word "about" may be omitted from the definition of the invention.

The term "treatment" includes any and all uses which remedy a disease state or symptoms, prevent the establishment of disease, or otherwise prevent, hinder, retard, or reverse the progression of disease or other undesirable symptoms in any way whatsoever. Hence, "treatment" includes prophylactic and therapeutic treatment.

Throughout this disclosure, certain embodiments may be disclosed in a range format. It should be understood that the description in range format is merely for convenience and brevity and should not be construed as an inflexible limitation on the scope of the disclosed ranges. Accordingly, the description of a range should be considered to have specifically disclosed all the possible sub-ranges as well as individual numerical values within that range. For example, description of a range such as from 1 to 6 should be considered to have specifically disclosed sub-ranges such as from 1 to 3, from 1 to 4, from 1 to 5, from 2 to 4, from 2 to 6, from 3 to 6 etc., as well as individual numbers within that range, for example, 1, 2, 3, 4, 5, and 6. This applies regardless of the breadth of the range.

DETAILED DESCRIPTION

The present invention provides the use of a composition that comprises at least 1, 2, 3, 4, 5, 6, 7, 8, 9, 10, 11, 12, 13, or 14, of the following components: Radix et Rhizoma Salviae Miltiorrhizae (Red Sage root or Dan Shen), *Prunus Persica* (Peach seed or Taoren), Radix Polygalae (root of thinleaf milkwort, *Polygala tenuifolia* Willd., *Polygala sibirica* L. or Yuanzhi), Buthus martensii (dried body of scorpio or Quanxie), Rhizoma acori Tatarinowii (rhizome of grassleaf sweetflag or Shichangpu), *Eupolyphaga Seu Seteleophaga* (dried body of ground beetle, *Eupolyphaga sinensis* Walker, *Steleophaga plancyi* or Tubiechong), Calculus Bovis Artifactus (Natural or Artificial cow-bezoar or Rengong Niuhuang), and Cornu Saigae Tataricae (Antelope Horn or Lingyangjiao) and combinations thereof, in the manufacture of a medicament for promoting neuronal outgrowth and proliferation of neurons or stem cells in tissues of the central or peripheral nervous system.

In one embodiment, the composition further comprises a second component selected from the group consisting of: Radix Astragali (root of Membranous Milkvetch or Huang Qi), Radix Paeoniae Rubra (Red Peony root, *Paeonia lactiflora* Pall, *Paeonia veitchii* Lynch or Chi Shao), rhizome of *Ligusticum Chuanxiong* (Chuan Xiong), Flower of *Carthamus Tinctorius* (Safflower or HongHua), radix *angelicae sinensis* (root of Chinese Angelica or DanGui) and dried body of leeches (*Hirudo*, *Whitmania pigra* Whitman, *Hirudo nipponica* Whitman *Whitmania acranulata* Whitman or Shuizhi) and combinations thereof.

The medicament promotes neuronal outgrowth and proliferation of neurons or stem cells in injured or diseased tissues which may occur patients with any of the following diseases: amyotrophic lateral sclerosis (ALS), brain abscess, brain ischemia, brain atrophy associated with diabetes, cerebral autosomal dominant arteriopathy with subcortical infarcts and leukoencephalopathy (CADASIL), cerebrovascular disorders, corticobasal ganglionic degeneration (CBGD), chronic ischemia, Creutzfeldt-Jakob Syndrome, Dandy-Walker Syndrome, Duchenne Muscular Dystrophy, senile dementia, dementia associated with Acquired Immunodeficiency Syndrome (AIDS), encephalomyelitis, essential tremor, friedreich ataxia, gerstmann straussler-scheinker disease, Huntington disease, hydrocephalus, hypoxia, fatal familial insomnia, transient ischemic attack, kuru, Landau-Kleffner Syndrome, Lewy body disease, Machado-Joseph disease, bacterial and viral meningitis, migraine disorders, myelitis, olivopotocerebellar atrophies, pantothenate kinase-associated neurodegeneration, poliomyelitis, postpoliomyelitis syndrome, prion diseases, pseudotumor cerebri, shy-drager syndrome, infantile spasms, progressive supranuclear palsy, Steinert disease, syringomyelia, thalamic diseases, Tic disorders, Tourette syndrome and Uveomeningoencephalitic syndrome.

The composition can also be used to treat patients having a condition selected from the group of psychiatric indications such as anxiety disorders, schizophrenia, depression and post-natal depression, natural aging, traumatic brain cell death and other neurologic manifestations such as amnesia, back pain, vertigo, unconsciousness, phantom limb, olfaction disorders, neck pain, headache, migranes, spasm and speech disorders.

In another embodiment, the composition may diminish the effect of stroke or neurodegeneration from predisposed subjects or subjects at risk of stroke or neurodegenration. The neurodegeneration may be caused by diseases selected from the group of Alzheimer's disease, amyotrophic lateral sclerosis (ALS), brain abscess, brain ischemia, brain atrophy associated with diabetes, cerebral autosomal dominant arteriopathy with subcortical infarcts and leukoencephalopathy (CADASIL), cerebrovascular disorders, corticobasal ganglionic degeneration (CBGD), chronic ischemia, Creutzfeldt-Jakob Syndrome, Dandy-Walker Syndrome, Duchenne Muscular Dystrophy, senile dementia, dementia associated with Acquired Immunodeficiency Syndrome (AIDS), encephalomyelitis, essential tremor, friedreich ataxia, gerstmann straussler-scheinker disease, Huntington disease, hydrocephalus, hypoxia, fatal familial insomnia, transient ischemic attack, kuru, Landau-Kleffner Syndrome, Lewy body disease, Machado-Joseph disease, bacterial and viral meningitis, migraine disorders, myelitis, olivopotocerebellar atrophies, pantothenate kinase-associated neurodegeneration, Parkinson's disease, poliomyelitis, postpoliomyelitis syndrome, prion diseases, pseudotumor cerebri, shy-drager syndrome, Steinert disease, infantile spasms, progressive supranuclear palsy, syringomyelia, thalamic diseases, Tic disorders, Tourette syndrome, Uveomeningoencephalitic syndrome, global and focal ischemia and other cardiovascular diseases, in predisposed subjects.

It is envisaged that NeuroAid™ or a NeuroAid™-like composition (e.g. a composition described below), optionally in combination with available supplemental agents that may be useful for the general well being of neurons or for the treatment of various nervous system diseases and other degenerative diseases. The supplemental agents may be vitamins, mineral supplements, herbal supplements, fish oils and Western medicine. Typically, the supplemental agent used in combination with NeuroAid™ or a NeuroAid™-like composition is one that targets a different mechanism from NeuroAid™ or a NeuroAid™-like composition. For example, the Western medicine may be growth factors typically used in improving recovery potential in the patients with degenerative diseases. Examples of suitable agents used in Western medicine include Calcium Channel Blockers (D-600, Diltiazem, Nitrendipine, Nimodipine, Nifedipine, Flunarizine, Fluspirilene, Isradipine, Nicardipine, PY 108-068, Verapamil and Triapamil), Calcium chelator (DP-b99), free radical scavengers (Ebselen, Tirilazad, NXY-059), GABA receptor agonists (Diazepam, Baclofen), AMPA agonists (ZK 200775/MPQX), competitive NMDA antagonists (aptiganel/cerestat, CP 101,606, dextrophan, MK 801/dizocilpine, remacemide), glycine site antagonists (GV 150526, ACEA 1021), polyamine site antagonists (eliprodil), growth factors (bFGF), Sodium channel blockers (fosphenytoin, 619C89), potassium channel opener (BMS 204352, cromakalim, levcromakalim, aprikalim, pinacidil, diazoxide, nicorandil, minoxidil), piracetam, adenosine transport inhibitor (propentofylline), gangliosides GM (non NMDA antagonist), presynaptic glutamate release inhibitors, clazosentan, desmoteplase, viprinex (ancrod), tenecteplase (TNKase; Metalyse), alteplase, cyclic nitrones, TWEAK (TNF-like weak inducer of apoptosis) receptor, thrombolytica treatments (urokinase, streptokinase, t-PA/ tissue plasminogen activator or recombinant urokinase), anistreplase, riluzole, and disufenton sodium (NXY 059), candesartan, AX-200 (G-CSF, Fligrastim), caffeinol (caffeine+ethanol), enecadin, microplasmin, sonolysis+tPA, V-10153, HTUPA, solulin, piclozotan, S-0139, 5-18986, AEOL-10150, AL-208, KN-38-7271, phridoxal 5-phosphate, Neu-2000KL, ONO-2231, PGX-100, RVX-208, SUN-N4057, SUN-N8075, TAT-NR2B9c, GLP-1-expressing stem cell therapy, Msc-1 (SA-4503, AGY-94806)), NH-02D, S-0139 259, tissue protective cytokines (Lu-AA24493), V10153 270 (BB-10153, TAPgen), combined use of statins and other cholesterol lowering drugs, erythropoietin, cerebrolysin and CDP-choline (cytidine-5'-diphosphocholine).

There is provided a method for inducing proliferation or differentiation of cells, comprising contacting said cells with an effective amount of at least one of the following components: Radix Astragali (root of Membranous Milkvetch or Huang Qi), Radix et Rhizoma Salviae Miltiorrhizae (Red Sage root or Dan Shen), Radix Paeoniae Rubra (Red Peony root, *Paeonia lactiflora* Pall, *Paeonia veitchii* Lynch or Chi Shao), rhizome of *Ligusticum Chuanxiong* (Chuan Xiong), radix *angelicae sinensis* (root of Chinese Angelica or DanGui), Flower of *Carthamus Tinctorius* (Safflower or HongHua), *Prunus Persica* (Peach seed or Taoren), Radix Polygalae (root of thinleaf milkwort, *Polygala tenuifolia* Willd., *Polygala sibirica* L. or Yuanzhi), *Buthus martensii* (dried body of scorpio or Quanxie), Rhizoma acori Tatarinowii (rhizome of grassleaf sweetflag or Shichangpu), dried body of leeches (*Hirudo, Whitmania pigra* Whitman, *Hirudo nipponica* Whitman, *Whitmania acranulata* Whitman or Shuizhi), *Eupolyphaga Seu Seteleophaga* (dried body of ground beetle, *Eupolyphaga sinensis* Walker, *Steleophaga plancyi* or Tubiechong), Calculus *Bovis* Artifactus (Natural or Artificial cow-bezoar or Rengong Niuhuang), and Cornu Saigae Tataricae (Antelope Horn or Lingyangjiao).

The composition may promote cell growth or cell survival would facilitate in vitro culture of various cells that may be used for tissue engineering or ex vivo therapeutic uses. In one embodiment, the patient receiving the cultured cells is also to be administered with NeuroAid™.

NeuroAid™ and Similar Compositions

The ingredients set forth above may be present in the composition in a relatively crude form (e.g. unprocessed or crushed herbs) or in a more refined form (e.g. purified extracts).

In one embodiment, NeuroAid™ from Moleac Pte Ltd is used. NeuroAid™ is a TCM product in capsule form comprising 9 herbal components and 5 animal components. NeuroAid™ comprises Radix Astragali (root of Membranous Milkvetch or Huang Qi), Radix et Rhizoma Salviae Miltiorrhizae (Red Sage root or Dan Shen), Radix Paeoniae Rubra (Red Peony root, *Paeonia lactiflora* Pall, *Paeonia veitchii* Lynch or Chi Shao), rhizome of *Ligusticum Chuanxiong* (Chuan Xiong), radix *angelicae sinensis* (root of Chinese Angelica or DanGui), Flower of *Carthamus Tinctorius* (Safflower or HongHua), *Prunus Persica* (Peach seed or Taoren), Radix Polygalae (root of thinleaf milkwort, *Polygala tenuifolia* Willd., *Polygala sibirica* L. or Yuanzhi), Rhizoma acori Tatarinowii (rhizome of grassleaf sweetflag or Shichangpu), *Buthus martensii* (dried body of scorpio or Quanxie), dried body of leeches (*Hirudo, Whitmania pigra* Whitman, *Hirudo nipponica* Whitman, *Whitmania acranulata* Whitman or Shuizhi), *Eupolyphaga Seu Seteleophaga* (dried body of ground beetle, *Eupolyphaga sinensis* Walker, *Steleophaga plancyi* or Tubiechong), Calculus *Bovis* Artifactus (Natural or Artificial cow-bezoar or Rengong Niuhuang), and Cornu Saigae Tataricae (Antelope Horn or Lingyangjiao).

In another embodiment, NeuroAid II comprises Radix Astragali (root of Membranous Milkvetch or Huang Qi), Radix et Rhizoma Salviae Miltiorrhizae (Red Sage root or Dan Shen), Radix Paeoniae Rubra (Red Peony root, *Paeonia lactiflora* Pall, *Paeonia veitchii* Lynch or Chi Shao), rhizome of *Ligusticum Chuanxiong* (Chuan Xiong), radix *angelicae*

*sinensis* (root of Chinese Angelica or DanGui), Flower of *Carthamus Tinctorius* (Safflower or HongHua), *Prunus Persica* (Peach seed or Taoren), Radix Polygalae (root of thinleaf milkwort, *Polygala tenuifolia* Willd., *Polygala sibirica* L. or Yuanzhi) and Rhizoma acori Tatarinowii (rhizome of grassleaf sweetflag or Shichangpu). NeuroAid™, which may be registered under different names in different countries (e.g. in South Africa it is marketed as Strocaid™ or Danqi Piantan Jiaonang™) is manufactured by and available commercially in the People's Republic of China from Tianjin Shitian Pharmaceutical Group Co., Ltd (located in the Jianxin Industrial area, Wangwenzhuang town, Xiqing district, Tianjin City, China; Postal Code 300381;). It is also available from Moleac Pte Ltd (formerly Molecular Acupuncture Pte Ltd), the main licensee outside of the People's Republic of China (11 Biopolis Way, Helios #09-08 Singapore 138667).

For the avoidance of doubt, NeuroAid™ not only includes NeuroAid™ in the form in which it is currently marketed but also includes future formulations of NeuroAid™ which may, for example, be marketed by Tianjin Shitian Pharmaceutical Group Co., Ltd or Moleac Pte Ltd. Such future formulations may, for example, vary in dosage amounts or the concentration of its active ingredients etc. NeuroAid™ is also known as MLC 601 and the terms "NeuroAid™" and "MLC 601" can be used interchangeably. Similarly NeuroAid II is also known as MLC 901 and the terms "NeuroAid II" and "MLC 901" can be used interchangeably.

Neuroprotectants

Using various mechanisms, neuroprotectants are compounds that preserve neuronal tissue at risk of dying during the course of diseases that adversely cause neurodegeneration. Some neuroprotectant agents include antioxidants (e.g. selenium, 30 vitamin E, vitamin C, glutathione, cysteine, flavinoids, quinolines, enzymes with; reducing activity, etc), N-methyl-D-aspartate Receptor Antagonists (Dextrorphan, Selfotel, Magnesium), Narcotic Receptor antagonist (Nalmefene (Cervene), Ca-channel blockers, Na-channel modulators (Lubeluzole), Alpha-aminobutyric acid agonist (Clomethiazole), glutamate receptor modulators, serotonin receptor agonists (repinotan), phospholipids, free-radical scavenger (Tirilazad, and NXY-059), astrocyte activation inhibitor (ONO 2506), monoclonal antibodies such as anti-ICAM-1 (Enlimomab), Human anti-leukocytic antibody, Hu23F2G, membrane stabilization agent CDP-choline (Citicholine), Fibroblast growth factor (Fiblast), unsaturated- and polyunsaturated fatty acids, estrogens and selective estrogen receptor modulators (SEAMS), progestins, thyroid hormone and thyroid hormone-mimicking compounds, cyclosporin A and derivatives, thalidomide and derivatives, methylxanthines, Mono-Amine-Oxydase inhibitors (IMAO), serotonin-, noradrenaline and dopamine uptake blockers, dopamine I agonists, L-DOPA, nicotine and derivatives, and NO synthase modulators.

Growth Factors

Using various mechanisms, growth factors are compounds that promotes particular cell to differentiate or proliferate. Some growth factors include bone morphogenetic proteins (BMPs), epidermal growth factor (EGF), erythropoietin (EPO), fibroblast growth factor (FGF), granulocyte-colony stimulating factor (G-CSF), granulocyte-macrophage colony stimulating factor (GM-CSF), hepatocyte growth factors (HGF), insulin-like growth factor (IGF), myostatin (GDF-8), nerve growth factor (NGF), neurotrophins, platelet-derived growth factor (PDGF), thrombopoietin (TPO), Transforming growth factor alpha (TGF-α), Transforming growth factor beta (TGF-β), vascular endothelial growth factor (VEGF), Interleukin-1β (IL-1β), IL-2, IL-3, IL-4, IL-6, IL-7, IL-8, IL-21, IL-33, M-CSF, Noggin, Interferons (IFN)-α, IFN-β and IFN-γ.

Compounds for Activating Potassium Channels TREK-1

Other suitable agents used in Western medicine include compounds capable of activating the potassium channels TREK-1. The activation of TREK-1 has been found to diminish the effects of stroke or neurodegeneration in predisposed subjects or subjects at risk of stroke or neurodegeneration. In addition, TREK-1 has been shown to play a role in treating patients with diseased or injured tissues of the central or peripheral nervous system, and patients suffering from depression, psychiatric indications, natural aging and traumatic brain cell death. Since NeuroAid® does not activate potassium channels TREK 1, compounds that are capable of activating the potassium channels TREK-1 may be used in combination with NeuroAid™ (MLC 601) to diminish the effects of stroke or neurodegeneration and treating patients with diseased or injured tissues of the central or peripheral nervous system, and patients suffering from depression, psychiatric indications, natural aging and traumatic brain cell death.

One example of a compound that is capable of activating the potassium channels TREK-1 is Polyunsaturated fatty acids (PUFAs). Polyunsaturated fatty acids are fatty acids that contain more than one double bond. PUFAs can be categorized as methylene-Interrupted Polyenes or Conjugated fatty acids.

Methylene-Interrupted Polyenes are fatty acids that have two or more cis double bonds that are separated from each other by a single methylene group. The essential fatty acids are all omega-3 and -6 methylene-interrupted fatty acids. Examples of Omega-3 fatty acids include without limitation: Alpha-linolenic acid (ALA), Stearidonic acid (STD), Eicosatrienoic acid (ETE), Eicosatetraenoic acid (ETA), Eicosapentaenoic acid (EPA), Docosapentaenoic acid (DPA), Docosahexaenoic acid (DHA), Clupanodonic acid, Tetracosapentaenoic acid, Tetracosahexaenoic acid or Nisinic acid. Examples of Omega-6 fatty acids include without limitation: Linoleic acid (LIN), Gamma-linolenic acid (GLA), Eicosadienoic acid, Dihomo-gamma-linolenic acid (DGLA), Arachidonic acid (AA), Docosadienoic acid, Adrenic acid, Docosapentaenoic acid or Osbond acid. Omega-9 fatty acids are also methylene-Interrupted polyenes, and may be monosaturated or polysaturated. Examples of Omega-9 fatty acids include without limitation: Oleic acid, Eicosenoic acid, Mead acid, Erucic acid or Nervonic acid.

Conjugated fatty acids are fatty acids that have two or more conjugated double bonds. Examples of Conjugated fatty acids include without limitation: Remenic acid, α-Calendic acid, β-Calendic acid, Jacaric acid, α-Eleostearic acid, β-Eleostearic acid, Catalpic acid, Punicic acid, Rumelenic acid, α-Parinaric acid, β-Parinaric acid, Bosseopentaenoic acid.

Some other PUFAs which are not catergorized as methylene-Interrupted Polyenes or Conjugated fatty include without limitation: Pinolenic acid and podocarpic acid.

Other compounds that may be capable of activating the potassium channels TREK-1 include the drug Riluzole (Rilutek®), Lysophospholids (LPLs), Caffeic Acid esters and Xenon. These compounds may also be used in combination with NeuroAid™ (MLC 601) to diminish the effects of stroke or neurodegeneration and treating patients with diseased or injured tissues of the central or peripheral nervous system, and patients suffering from depression, psychiatric indications, natural aging and traumatic brain cell death.

Modes of Administration

NeuroAid™ (MLC 601) may be administered orally, parenterally, intravenously, subcutaneously, intradermally, intraperitoneally or topically, in liquid, semi-liquid or solid form and are formulated in a manner suitable for each route of administration. When NeuroAid™ (MLC 601) is administered orally, it may be administered as four 0.4 g capsules being taken 3 times a day. For patients with swallowing difficulties, capsules may be opened and powder diluted in water that can be drunk as such or injected via a gastric tube. Hence, a daily dose of about 4.8 g is envisaged. In one embodiment, the patient's daily dose of NeuroAid™ (MLC 601) is about 1 g to 8 g; 2 g to 8 g; 3 g to 7 g; 4 g to 6 g; 4.25 g to 5.75 g; 4.5 g to 5.25 g; 4.5 g to 5 g; 4.6 g to 4.10 g; or 4.7 g to 4.9 g. A "daily dose" can be a single tablet or capsule etc. or multiple tablets or capsules etc. to be taken on a given day.

In one embodiment, each course of NeuroAid™ (MLC 601) treatment lasts about 4 weeks. Typically 3 courses are administered, most commonly back to back. No therapeutic window is required but additional courses can be added even after a few days of treatment cessation. Hence, in one embodiment, each NeuroAid™ (MLC 601) treatment lasts about 12 weeks. In another embodiment, the treatment course of NeuroAid™ (MLC 601) is about 4 to 24 weeks; 7 to 16 weeks; 9 to 15 weeks; 10 to 14 weeks; or 11 to 13 weeks.

In another embodiment, NeuroAid™ (MLC 601) can also be used as a chronic treatment to address chronic disease or as a preventive measure.

In one embodiment, NeuroAid™ (MLC 601) may be used as part of a combination therapy with western medicine that promotes cell growth. The combination partners of NeuroAid™ (MLC 601) and cell growth factor may be present in a single formulation or may be present as separate formulations. In one embodiment there may be a synergistic effect.

The combination partners NeuroAid™ (MLC 601) and cell growth factor may be administered to the patient at the same time (e.g. simultaneously) or at different times (e.g. sequentially) and over different periods of time, which may be separate from one another or overlapping. The combination partners NeuroAid™ (MLC 601) and cell growth factor may be administered in any order.

When cell growth factor is utilized and the appropriate administration route and dose level will be known to those in the art or could be readily determined by one skilled in the art. Typically, as is well known in the medical art, dosage regimens may depend on various factors including the patient's size, body surface area, age, the particular compound to be administered, sex, time and route of administration, general health, and other drugs being administered concurrently. While individual needs vary, determination of optimal ranges of effective amounts of each component is within the skill of the art. The dosage would be similar to that administered when the agent is used without NeuroAid™ (MLC 601).

BRIEF DESCRIPTION OF DRAWINGS

FIG. 7A shows the experimental protocol for Example 4, which investigates the effects of NeuroAid II (MLC 901) treatment; FIG. 7B shows the experimental protocol for Example 5, which investigates the effects of an acute NeuroAid II (MLC 901) treatment. Both studies assessed the rate of survival and also quantified the infarct volume at 24 h post-ischemia.

FIG. 10A shows the effect of the respective treatments on cell viability and FIG. 10B shows the effect of the respective treatments on LDH release.

FIG. 11A and FIG. 11B shows the survival rate (A) and infarct volume (B) respectively.

FIG. 12A and FIG. 12B shows the survival rate (A) and infarct volume (B) respectively.

EXAMPLES

Figure 1:
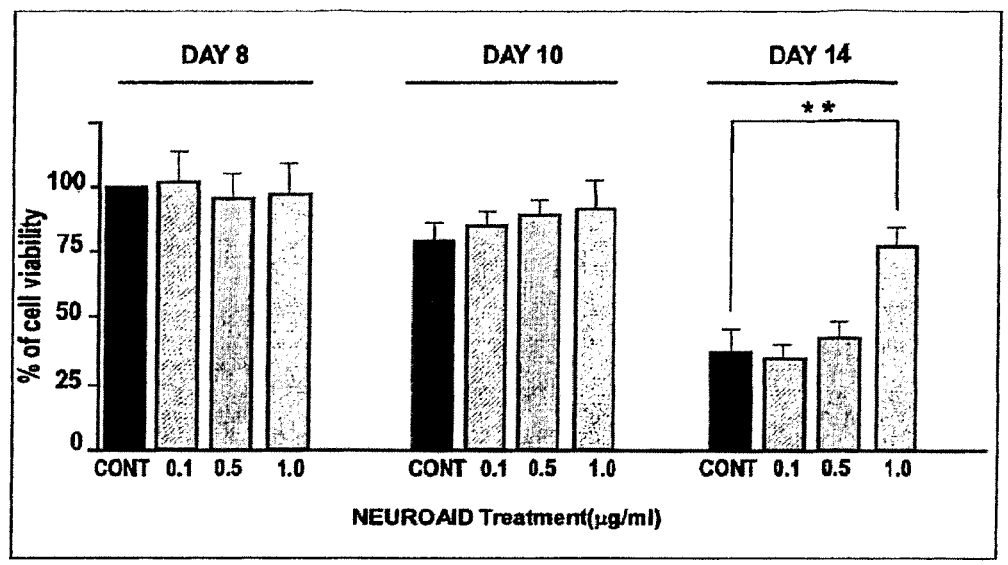
FIG. 1 shows bar charts of the dose-effect of NeuroAid™ (MLC 601) treatment on cell viability on day 8, day 10 and day 14. Three concentrations of NeuroAid™ (MLC 601) (0.1, 0.5, 1.0 µg/ml) were compared to the control.

Non-limiting examples of the invention will be further described in greater detail by reference to specific examples, which should not be construed as in any way limiting the scope of the invention.

Materials

Medium for Cortical Sampling:
  HBSS/1
  NaCl 8 g/l
  KCl 0.26 g/l
  MgSO$_4$ 0.2 g/l
  CaCl$_2$ 0.264 g/l
  NaH$_2$CO$_3$ 2.24 g/l
  NaH$_2$PO$_4$ 0.15 g/l in H$_2$O
  HBSS+: add 6 g glucose Cell Culture Medium
  Neurobasal (21103-049; Invitrogen, San Diego, Calif.)
  qB27 (no 17504; Invitrogen, San Diego, Calif.)
  Uridine (U3003; Sigma, St. Louis, Mo., USA)
  Fluoro-deoxy-Uridine (46875; Fluka-Chemika-Biochemika, Buchs, Switzerland)
  Glutamax (35050; Gibco-BRL Life Technologies. GmbH, Karlsrahe, Germany)
  Antibiotics (Penicillin-streptomycin) (Gibco-BRL Life Technologies. GmbH, Karlsrahe, Germany)

Animals

All experiments were performed according to policies on the care and use of laboratory animals of European Community legislation. The local Ethics Committee approved the experiments (protocol numbers NCA/2006/10-1 and NCA/2006/10-2). Adult male C57/Bl6 mice, weighing 22 to 26 g were used in this study. The animals housed under controlled laboratory conditions with a 12-hour dark-light cycle, a temperature of 21±2° C., and a humidity of 60 to 70% for at least one week prior to drug treatment or surgery. The mice had free access to standard rodent diet and tap water.

NeuroAid II (MLC 901) Drinking Solution

One capsule of NeuroAid II (MLC 901) was dissolved in 66 ml water under stirring with an agitator for one hour at 37° C. The solution is then filtered with a 0.45 μm filter.

NeuroAid II (MLC 901) for Intraperitoneal Injections 30 mg from a NeuroAid II (MLC 901) capsule was diluted in 3 ml saline solution corresponding to a concentration of 10 mg/ml (Stock solution) at 37° C. during 60 min. The concentration used in the experiment is 1 μg/ml (injected volume: 500 μl). To obtain the dose of 1 μg/ml, the stock solution is diluted by 100. After dilution, the mixture is vortexed to obtain a good homogenization and filtered on a 0.45 μm filter.

Methods

A. Cortical Cell Culture

Time-pregnant (E14) C57Bl6/J mice were anesthetized with isopentane followed by cervical dislocation. Fetuses were removed and placed in cold (Hanks Balanced Salt Solution) HBSS+ solution. Cerebral cortices were dissected in cold HBSS+ solution and the meninges were removed. The cortical samples were cut in small pieces and were gently triturated with a fire-polished glass Pasteur pipette in 8 ml HBSS+ solution. The mix was filtered (40 μM filter) and centrifuged at 800 rpm for 8 min. The supernatant was removed and the pellet was dissolved in 2 ml culture medium. Cells were plated on Polylysine-coated 12 well (24 mm diameter; Sigma-Aldrich Chimie, St. Quentin Fallavier, France)) plates with glass coverslips (12 mm diameter; CML, Nemours, France) at a density of 1×10$^6$ cells/well. Cultures were maintained at 37° C. in a humidified 5% CO$_2$ atmosphere incubator in Neurobasal supplemented with B27, Glutamax, antibiotics were used for experiments after 16 days. Glial growth was suppressed by addition of 5-Fluoro-2-deoxyuridine (2 μM) and Uridine (2 μM) during the second day of culture.

B. Neuroaid™ (MLC 601) Treatment 30 mg from a NeuroAid™ (MLC 601) capsule was diluted in 3 ml Neurobasal medium corresponding to a concentration of 10 mg/ml (Stock solution) at 37° C. for a duration of 60 minutes. The concentrations tested in the experiments were: 1 μg/ml or 10 μg/ml of culture medium. 1 ml of NeuroAid™ (MLC 601) solution was put in each 24 mm well of plate.

To obtain the dose of 1 μg/ml, the stock solution was diluted by 100 times: 0.1 mg/ml (10 μl per 24 mm well/ml, corresponding to 1 μg/well).

To obtain the dose of 10 μg/ml, the stock solution was diluted by 10 times: 1 mg/ml (10 μl per 24 mm well/ml, corresponding to 10 μg/well).

After dilution, the mixture was vortexed to obtain a good homogenization and filtered on a 0.45 μm filter.

Cells were treated each day with NeuroAid™ (MLC 601), NeuroAid II (MLC 901) or Neurobasal medium from Day 1 of culture.

C. Lactate Dehydrogenase (LDH) Measurements

Neuronal injury was quantitatively assessed by the measurement of lactic dehydrogenase (LDH) release from cultured neurons incubated in cell culture medium. At Day 1, 5, 8, 10, 12, 14 and 16, 100 μl of the cell culture medium was transferred from culture wells to 96-well plates and mixed with 100 μl of reaction solution according to LDH assay kit (Roche Diagnostic: Cytotoxicity Detection kit: ref 1644793, Indianapolis, USA). Optical density (OD) was measured 30 minutes later at 492 nm utilizing a Labsystem Multiscan microplate reader (Labsystem Multiscan RC, Finland). Background absorbance at 620 is subtracted. LDH activity is expressed as activity present in the 25 μl medium volume. Results are expressed as OD×10$^{-3}$.

D. Cell Viability

At Day 1, 5, 8, 10, 12, 14 and 16, the totality of cell culture medium was removed and replaced by 500 μl of Neurobasal medium+Cell Titer 96 Aqueous One Solution kit: Cell Titer 96 (r) Aqueous One Solution Cell Proliferation Assay Kit. Neuronal viability was determined using the Cell Titer 96 (r) Aqueous One Solution Cell Proliferation Assay (Promega, Madison, USA). According to the Proliferation Assay Kit protocol, cells are incubated for 4 hours at 37° C. in the humidified 5% CO$_2$ atmosphere incubator. The reaction was stopped with 2% Sodium Dodecyl Sulfate (SDS). Optical density was measured 4 hours later at 490 nm utilizing a Labsystem Multiscan microplate reader. Background absorbance at 620 was subtracted. Results were expressed as OD×10$^{-3}$ representing the number of viable cells.

Statistic analysis of cell viability and LDH results are assessed using one factor (analysis of variance) ANOVA test followed by post-hoc test (P<0.05).

E. Double Cortin (DCX) Immunohistochemistry of Cortical Cell on Coverslips

Cortical cell are fixed onto coverslips with 4% paraformaldehyde in phosphate buffered saline (PBS), permeabilized in 0.3% polyoxyethylensorbitan monolaurate (Tween 20, Sigma) for 10 minutes and blocked with 2.5% donkey serum in PBS for 2 hours at room temperature. Coverslips were incubated with a goat anti-doublecortin (DCX) antibody (1:200, SC-8066, Santa Cruz Biotechnology Inc., Santa Cruz, Calif.) in 2% donkey serum/PBS overnight. After 3 washes in PBS, coverslips were incubated in anti-goat Alexa 488-coupled antibodies (FluoProbes, Interchim, Montlugon, France) in 2% donkey serum for 2 hours, and washed three times in PBS for 5 min each. The coverslips are then incubated in Hoechst solution (3 µl in 10 ml; Sigma-Aldricht Chimie, Saint Quentin Fallavier, France) for 10 minutes to label cell nuclei. After 2 washes in PBS and 1 wash in water, the coverslips are dried and mounted on glass slides with Fluoroprep (75521; BioMérieux, Marcy l'Etoile, France). Cells were observed using epifluorescence and confocal microscopy. Confocal microscopy observations are performed using a Laser Scanning Confocal Microscope (TCS SP, Leica Microsystems Heidelberg GmbH, based in Mannheim, Germany) equipped with a DMIRBE inverted microscope and an argon-krypton laser (laser excitation 488 nm, acquisition 500-600 nm every 10 nm). Signal specificity was assessed in negative control coverslips by omitting primary antibody directed against the DCX protein. Images were acquired as single transcellular optical sections and averaged over at least four scans per frame. Confocal images of DCX-Alexa-488 antibody labeling were then obtained after spectral correction of the autofluorescence background.

F. Physiological Parameters Used when Investigating the Effects of a NeuroAid II (MLC 901) in C57Bl/6 mice General anesthesia was induced with 3% isoflurane and maintained with 1% isoflurane by means of an open facemask for each mouse. Mice were allowed to breathe spontaneously. A subset of animals (n=5 per group) were monitored for physiological parameters including mean arterial blood pressure (MABP), rectal temperature, arterial blood gases and pH before, during and after ischemia. The right femoral artery was catheterized with PE-10 polyethylene tubing and connected to a blood pressure transducer (Harvard Apparatus, Massachusetts, USA) for continuous monitoring of MABP (mm Hg). A heparinized blood sample (75 µl) was then obtained from the catheterized femoral artery and blood $pO_2$, $pCO_2$ and pH were measured using an Acid-Base Laboratory system (ABL 555, Radiometer). Core temperature was monitored continuously with a thermometer (3-mm probe diameter; Harvard Apparatus, Massachusetts, USA), inserted into the rectum and maintained at physiological temperatures using a thermostatically controlled heating blanket (Harvard Apparatus, Massachusetts, USA). Core temperature was maintained at physiological values by a combination of the homeothermic blanket control.

G. Induction of Transient Focal Cerebral Ischemia in C57Bl/6 Mice

Focal ischemia was induced by occlusion of the left middle cerebral artery (MCA) using an intraluminal filament technique (Heurteaux et al, 2006) After a midline neck incision was made, the left common and external carotid arteries were isolated and ligated with a silk 4-0 silk suture (Ethicon). A temporary yasargil aneurysm clip (BMH31, Aesculap, Tuttlingen, Germany) was temporarily placed on the internal carotid artery. A 6-0 coated filament (Doccol, Redlands, Calif., USA), blunted at tip with an open flame, was introduced through a small incision into the common carotid artery and 13 mm distal to the carotid bifurcation for occlusion of the origin of the MCA. Animals were kept at 37° C. for one hour, after which time the thread was carefully withdrawn to allow reperfusion of the MCA territory. To control the MCAO severity regional CBF (rCBF) was determined by laser-Doppler flowmetry (Perimed) using a flexible 0.5-mm fiber optic extension to the masterprobe fixed on the intact skull over the ischemic cortex (2 mm posterior and 6 mm lateral from the bregma). Sham-operation was performed inserting the thread into the common carotid artery without advancing it to occlude the MCA. The animals were allowed to regain full consciousness on a heating pad before returning to the cage.

H. Determination of Infarct Volume

To assess the infarct volume in the acute NeuroAid II (MLC 901) post-treatment study (Example 5), mice were sacrificed at 24 hours after reperfusion. Their brains were removed and sectioned into six 1 mm-thick coronal slices using a tissue chopper (Phymep, France). Coronal brain slices were immediately immersed into 2% 2, 3, 5-Triphenyltetrazolium chloride (TTC, Sigma, France) for 20 min at room temperature in the dark followed by fixation in a 4% paraformaldehyde solution overnight prior to analysis as described previously (Ding-Zhou et al., 2002). The striatal and cortical areas of infarction, outlined in light were measured on each section using a computer image analysis system and corrected for brain edema according to Golanov and Reis (Golanov and Reis, 1995). Infarct volume, expressed in $mm^3$ was calculated by a linear integration of the corrected lesions areas.

In addition cresyl violet, a dye that stains the Nissl bodies in the stellate somas of viable neurons was used to confirm the evolution of infarct volume in ischemic mice. Coronal frozen sections of brain (10 µm-thick) were added to a solution of 1% cresyl violet in 0.25% acetic acid for 3 min, rinsed, dehydrated and mounted with Entellan. Sections were analyzed under light microscopy.

Example 1

Dose-Effect of NeuroAid™ (MLC 601) on Cell Viability and LDH Release

Cortical cells, as prepared by the methods disclosed above, were exposed to four concentrations of NeuroAid™ (MLC 601): 0.1, 0.5, 1.0, 10 µg/ml from Day 1 until Day 14 of culture. Cell viability was studied at Day 8, 10 and 14 by the methods disclosed above and the results are shown in FIG. 1.

The effect of NeuroAid™ (MLC 601) treatment against neurodegeneration of cortical cells over time in culture was also analyzed by LDH release. Increasing cell suffering that leads to cell death is associated with increased LDH release. LDH release was measured on day 10 and day 14 by the methods disclosed above and the results are shown in FIG. 2.

Results

FIG. 1 shows that at Day 14, a NeuroAid™ (MLC 601) treatment at a concentration of 1 µg/ml induced a significant increase (35%) in neuronal survival as compared to control (**$P<0.01$). Until Day 10 there was no significant difference in the percentage of cell viability on cells treated with NeuroAid™ (MLC 601) concentrations of 0.1-0.5-1.0 µg/ml as compared to control ($P>0.05$) (n=10 wells per experimental group).

Figure 2:
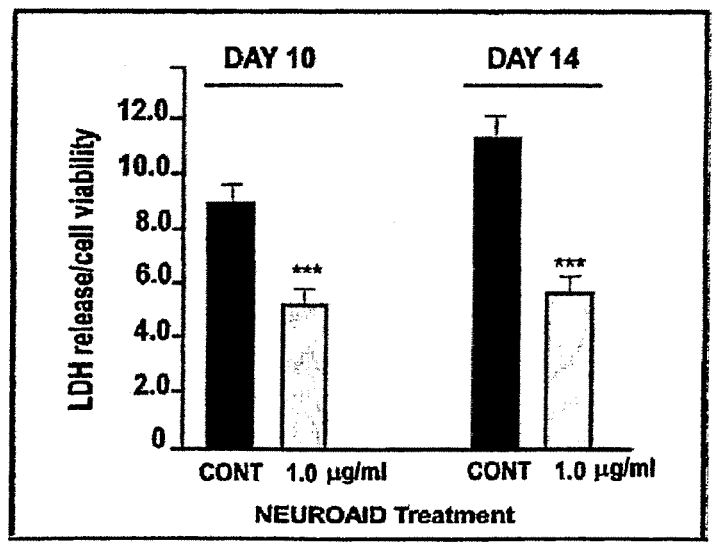
FIG. 2 shows bar charts of the effect of NeuroAid™ (MLC 601) treatment on LDH release on day 10 and day 14. A concentration of 1.0 µg/ml NeuroAid™ (MLC 601) was compared to the control.

FIG. 2 shows the ratio of LDH release/cell viability at Day 10 and 14 at the concentrations of 1 µg/ml NeuroAid™ (MLC 601). Compared to control, NeuroAid™ (MLC 601) treatment significantly reduced the LDH release after 10 and 14 days of culture ($P<0.01$) (n=10 wells per experimental group).

Based on the experimental data in Example 1, it can be demonstrated that treatment with NeuroAid™ (MLC 601) in cortical cells in culture demonstrates an increase of cell viability and a reduction of LDH release, which is a marker of the cell suffering. Example 1 also demonstrates that NeuroAid™ (MLC 601) may be used for diminishing the effect of stroke or neurodegeneration in predisposed subjects or subjects at risk of stroke or neurodegeneration, for treating patients with diseased or injured tissues of the central or peripheral nervous systems, or for use as a cell culture reagent.

Example 2

Effect of NeuroAid™ (MLC 601) on Neuronal Proliferation/Neurogenesis

DCX is a highly hydrophilic microtubule-associated protein that was expressed specifically in all migrating precursors of the developing CNS and in areas of continuous neurogenesis in adult brain. Neuronal proliferation was analyzed from DCX expression in cortical cells in culture by the methods disclosed above. Cortical cells, as prepared by the methods disclosed above, were treated with 1 μg/ml NeuroAid™ (MLC 601) from Day 1 until Day 14 of culture. The cells were then prepared and observed using epifluorescence and confocal microscopy as described in the methods above to determine DCX expression. The results are shown in FIG. 3.

Results

Figure 3:
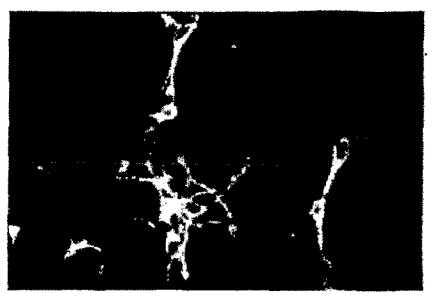
FIG. 3 shows confocal images of the effect of NeuroAid™ (MLC 601) treatment on neuronal DCX expression on day 3 and day 14. A concentration of 1.0 µg/ml NeuroAid™ (MLC 601) was compared to the control.
Figure 3:
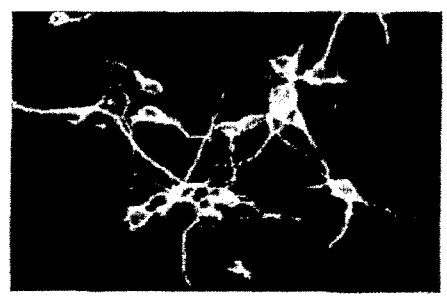
Figure 3:
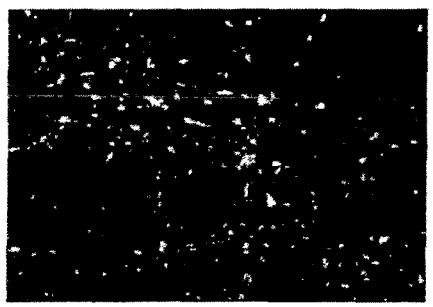
Figure 3:
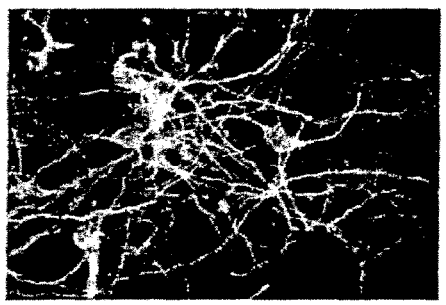
Figure 3:
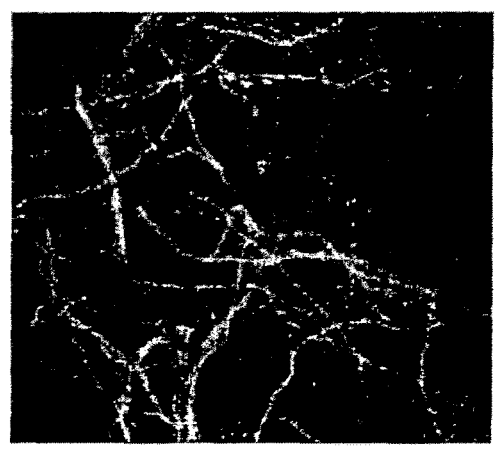

In FIG. 3, staining with an antibody against DCX shows that at Day 3, there was no difference in DCX expression between the control and cortical cells treated with 1 μg/ml NeuroAid™ (MLC 601). However, at Day 14, DCX immunoreactivity disappeared in the control, while there was an increase of DCX expression induced by NeuroAid™ (MLC 601) treatment, highlighting the development of an important axonal and dendritic network.

Because of its association with neurogenic processes, the DCX protein is currently used as a marker for neurogenesis. DCX is a microtubule-associated protein whose expression is associated with all migrating neuronal precursors in fetal and adult brain. DCX appears to be important for the normal developmental migration of cortical neurons, because mutations in DCX in humans lead to syndromes characterized by migrational arrest of these neurons and which is manifested clinically by subcortical laminar heterotopias, mental retardation and seizures. DCX is also expressed in some mature neurons in the adult brain, where it is involved in axonal outgrowth and synaptogenesis.

Thus, based on the experimental data of Example 2, it can be demonstrated that treatment with NeuroAid™ (MLC 601) results in an increase in DCX expression in cortical cells, suggesting strongly that treatment with NeuroAid™ (MLC 601) enhances neuroproliferation, neurogenesis, and neurorepair necessary to restore neurological function (such as motor and cognitive). Example 2 also demonstrates that NeuroAid™ (MLC 601) may be used for promoting neuronal outgrowth and proliferation of neurons in tissues of the central or peripheral nervous systems, for promoting cell growth, and for a method for inducing cell survival, growth, proliferation or differentiation of cells using NeuroAid™ (MLC 601).

Example 3

Effect of NeuroAid™ (MLC 601) and NeuroAid II (MLC 901) Treatments on Cell Viability, LDH Release and Neuronal Proliferation Cortical cells were exposed to a concentration of 1 μg/ml NeuroAid™ (MLC 601) or NeuroAid II (MLC 901) from Day 1 until Day 14 of culture. This concentration of 1 μg/ml corresponds to the best results obtained on cell viability and LDH release as described above. Cell viability was studied at Day 8, 10, 12 and 14. Neuronal proliferation in the course of time was analyzed by observing DCX expression in cortical cells in culture treated with 1 μg/ml NeuroAid™ (MLC 601) or NeuroAid II (MLC 901).

Results

Figure 4:
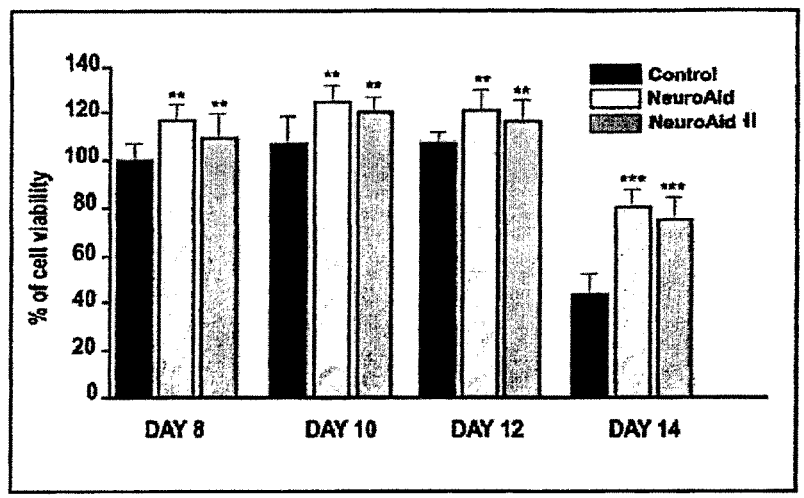
FIG. 4 shows bar charts of the effect of NeuroAid™ (MLC 601) and NeuroAid II (MLC 901) treatments on cell viability on day 8, day 10, day 12 and day 14. A concentration of 1.0 µg/ml NeuroAid™ (MLC 601) and 1.0 µg/ml NeuroAid II (MLC 901) were compared to the control.

FIG. 4 shows that at Day 8, a significant increase in neuronal viability as compared to respective control ($P<0.01$; *$P<0.001$) was observed in cortical cells treated with 1 μg/ml NeuroAid™ (MLC 601) or NeuroAid II (MLC 901). However, the highest efficiency of both treatment was observed at Day 14 with ~45% increase of cell survival (***$P<0.001$). There was no significant difference of efficiency between NeuroAid™ (MLC 601) and NeuroAid II (MLC 901) at the different stages of culture (n=10 wells per experimental group).

Figure 5:
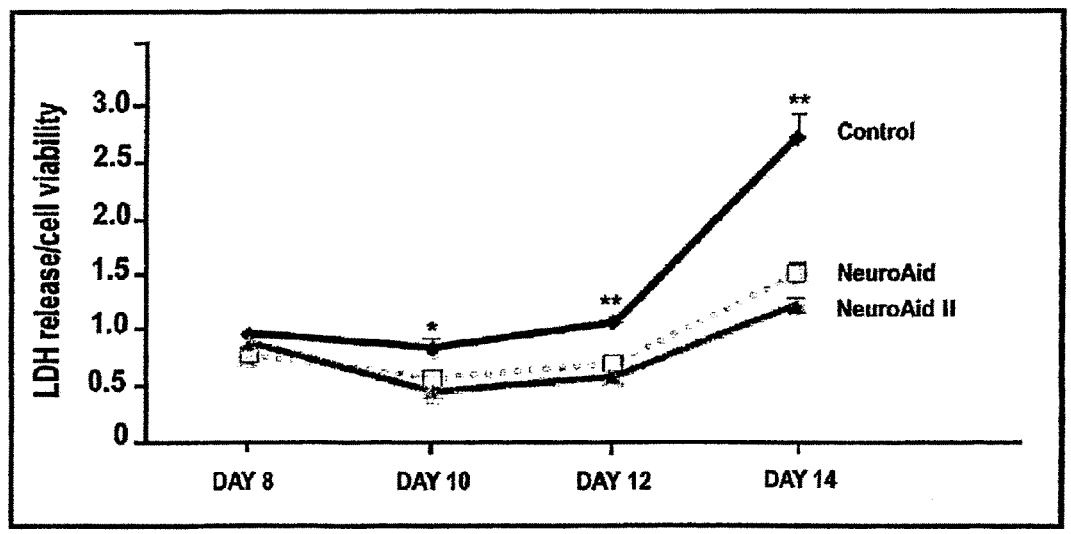
FIG. 5 shows a line graph of the effect of NeuroAid™ (MLC 601) and NeuroAid II (MLC 901) treatments on LDH release on day 8, day 10, day 12 and day 14. A concentration of 1.0 µg/ml NeuroAid™ (MLC 601) and 1.0 µg/ml NeuroAid II (MLC 901) were compared to the control.

FIG. 5 shows the comparison of NeuroAid™ (MLC 601) and NeuroAid II (MLC 901) treatments on the ratio of LDH release/cell viability at Day 8, 10, 12 and 14 at the concentrations of 1 μg/ml. Compared to the control, both treatments significantly reduced LDH release after 12 and 14 days of culture (*$P<0.05$ and ***$P<0.001$) (n=10 wells per experimental group). There was no significant difference of efficiency on LDH release between NeuroAid™ (MLC 601) and NeuroAid II (MLC 901) treatments.

Figure 6:
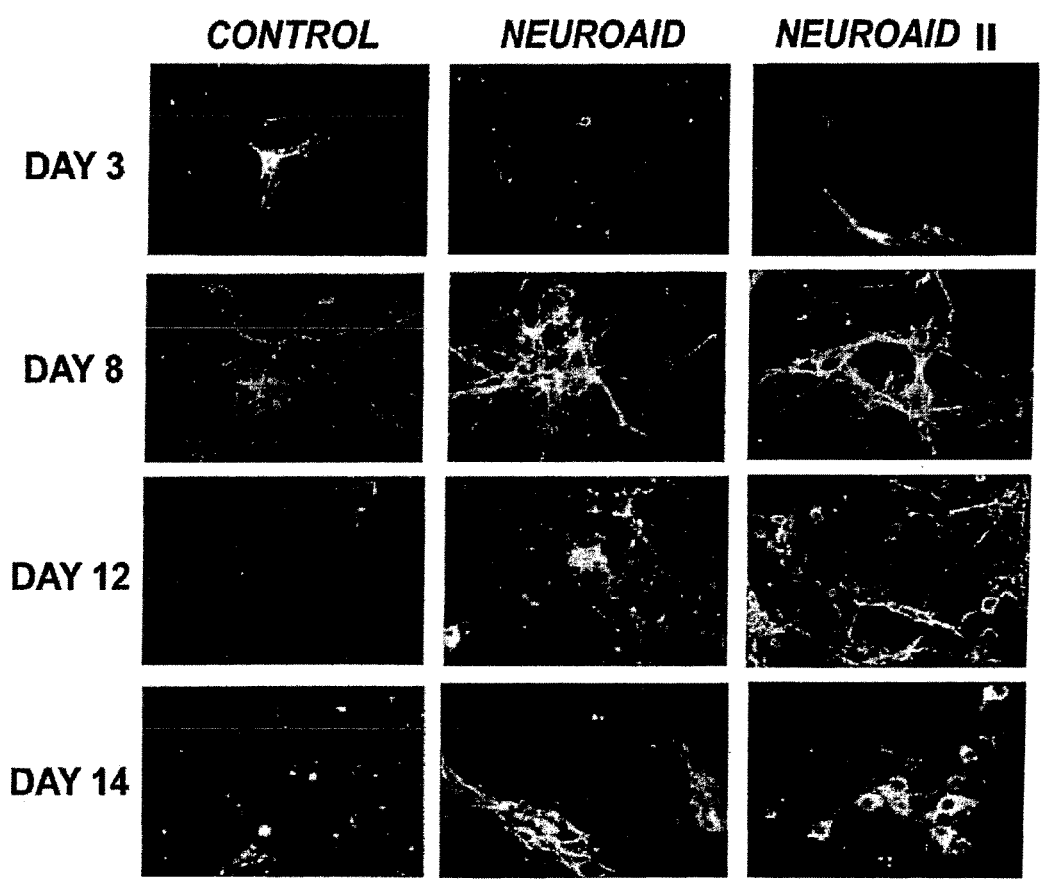
FIG. 6 shows confocal images of the effect of NeuroAid™ (MLC 601) and NeuroAid II (MLC 901) treatments on DCX expression on day 3 and day 14. A concentration of 1.0 µg/ml NeuroAid™ (MLC 601) and 1.0 µg/ml NeuroAid II (MLC 901) were compared to the control.

FIG. 6 shows that, compared to the control, cortical cells treated with 1 μg/ml NeuroAid™ (MLC 601) or NeuroAid II (MLC 901) developed a much denser axonal and dendritic network from Day 3 in culture. At Day 14, DCX immunoreactivity disappeared in Control and the labeling of the DCX protein became different between cortical cells treated with NeuroAid™ (MLC 601) and cortical cells treated with NeuroAid II (MLC 901). The DCX protein was always expressed in processes of cortical cells treated by NeuroAid™ (MLC 601) or NeuroAid II (MLC 901). However, it appeared that in cortical cells treated with NeuroAid II (MLC 901), there was also a strong increase of DCX immunoreactivity in the cytoplasm of these cells.

The results obtained with both NeuroAid™ (MLC 601) treatments (NeuroAid™ (MLC 601) and NeuroAid II (MLC 901)) show an increase in cell survival, an increase in LDH release and an increase of DCX expression in cortical cells. There was no significant difference between the results of NeuroAid™ (MLC 601) and NeuroAid II (MLC 901). Thus, based on the experimental data, it can be demonstrated that both NeuroAid™ (MLC 601) treatments (NeuroAid™ (MLC 601) and NeuroAid II (MLC 901)) enhance neuroproliferation, neurogenesis and neurorepair and may be a form of enhanced treatment for neurological diseases and nervous system injuries.

The experimental results above also support the use of extracts of NeuroAid™ (MLC 601) and NeuroAid II (MLC 901) for improvement of connectivity and survival of all types of neuronal cultures. These extracts could be systematically added to classical culture media for neuronal cultures to considerably improve viability, dendritic growth and synaptogenesis. Example 3 also demonstrates that (NeuroAid™ (MLC 601) and NeuroAid II (MLC 901) may be used for promoting neuronal outgrowth and proliferation of neurons in tissues of the central or peripheral nervous systems, for promoting cell growth, for treating patients having a condition selected from the group of depression, psychiatric indications, natural aging and traumatic brain cell death, diminishing the effect of stroke or neurodegeneration in predisposed subjects or subjects at risk of stroke or neurodegeneration, promotin cell growth, for treating patients with diseased or injured tissues of the central or peripheral nervous systems, for use as a cell culture reagent and for a method for inducing cell survival, growth, proliferation or differentiation of cells.

Example 4

The Effect of NeuroAid II (MLC 901) Pretreatment in Mice 24 h Post-Ischemia

Figure 7:
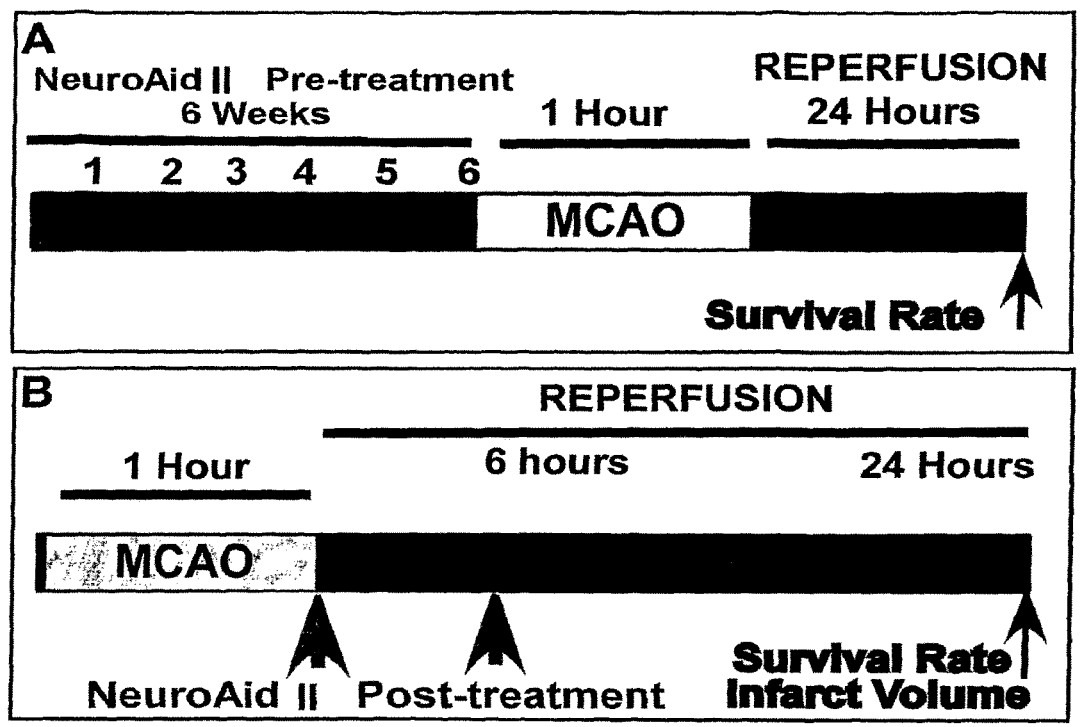
FIG. 7 shows schematic diagrams of the experimental protocols for NeuroAid II (MLC 901) treatments against stroke.

In this study, mice (n=11) were pretreated for six weeks with a drinking solution of NeuroAid II (MLC 901) and the rate of survival was analyzed at 24 h post-ischemia (FIG. 7A). Control mice (n=10) received a tap water drinking solution.

Figure 8:
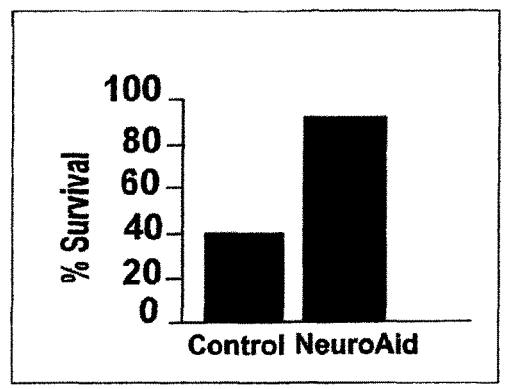
FIG. 8 shows a bar graph of the survival rate after NeuroAid II (MLC 901) pre-treatment at 24 h post-ischemia.

To determine whether a pretreatment of NeuroAid II (MLC 901) increases the rate of survival of mice subjected to ischemia, the animals were treated with NeuroAid II (MLC 901) during six weeks before the induction of ischemia. FIG. 8 shows that a six week-pretreatment of NeuroAid II (MLC 901), given in the drinking induced a strong reduction of the mortality of NeuroAid II (MLC 901)-treated animals, compared to control mice. The NeuroAid II (MLC 901) pretreatment during six weeks induced a survival rate of 90.9% as compared to 40.0% in control group.

Example 4 demonstrates that NeuroAid is beneficial before an ischemic stroke. These studies illustrates that NeuroAid advantageously reduced the infarct size and mortality rate of ischemic mice in a clinically relevant model of stroke.

Example 5

The Effect of Acute NeuroAid II (MLC 901) Post-Treatment in Mice 24 h Post-Ischemia In this study, mice (n=10) received an acute post-treatment intraperitoneal injection of NeuroAid II (MLC 901), given at the onset of ischemia and 6 h after reperfusion. Control mice (n=10) was injected with saline solution. The survival rate and the infarct volumes were quantified at 24 h of reperfusion.

Figure 9:
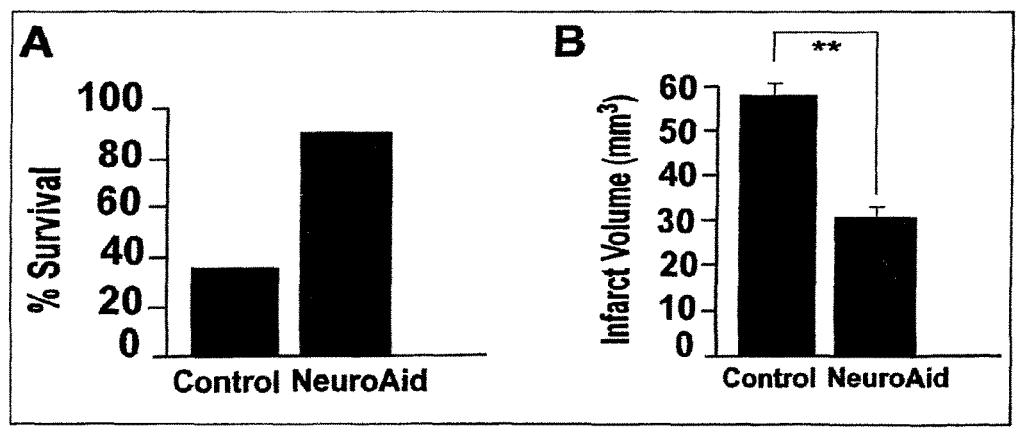
FIG. 9 shows a bar graph of the survival rate (A) and infarct volume (B) after NeuroAid II (MLC 901) post-treatment at 24 h post-ischemia.

To determine whether acute administration of NeuroAid II (MLC 901) protects against ischemic stroke, mice (n=10) were subjected to ischemia and injected intraperitonally with a single dose of 1 mg/ml of NeuroAid II (MLC 901) solution at the onset of ischemia and 6 h after reperfusion. Acute administration of NeuroAid II (MLC 901) induced a survival rate of 90.0% compared to 38.8% observed in control mice (FIG. 9A). This NeuroAid II (MLC 901) post-treatment drastically decreased cerebral infarction as shown in FIG. 9B. The NeuroAid post-treatment reduced the stroke volume by 47.4% (P<0.001) as compared to control mice.

These studies demonstrate that NeuroAid is beneficial both before and after an ischemic stroke. These studies illustrates that NeuroAid advantageously reduced the infarct size and mortality rate of ischemic mice in a clinically relevant model of stroke.

Methods for Examples 6 to 8

A. Cortical Cell Culture

Time-pregnant (E14) C57Bl6/J mice were anesthetized with isopentane followed by cervical dislocation. Fetuses were removed and placed in cold (Hanks Balanced Salt Solution) HBSS+ solution. Cerebral cortices were dissected in cold HBSS+ solution and the meninges were removed. The cortical samples were cut in small pieces and were gently triturated with a fire-polished glass Pasteur pipette in 8 ml HBSS+ solution. The mix was filtered (40 µM filter) and centrifuged at 800 rpm for 8 min. The supernatant was removed and the pellet was dissolved in 2 ml culture medium. Cells were plated on Polylysine-coated 12 well (24 mm diameter; Sigma-Aldrich Chimie, St. Quentin Fallavier, France)) plates with glass coverslips (12 mm diameter; CML, Nemours, France) at a density of $1 \times 10^6$ cells/well. Cultures were maintained at 37° C. in a humidified 5% $CO_2$ atmosphere incubator in Neurobasal supplemented with B27, Glutamax, antibiotics were used for experiments after 16 days. Glial growth was suppressed by addition of 5-Fluoro-2-deoxyuridine (2 µM) and Uridine (2 µM) during the second day of culture.

Experiments were monitored by one researcher blinded to the treatment status (n=3 cultures, 36 wells per experimental group).

B. Cell Injury Assay: Cell Survival and Lactate Dehydrogenase (LDH) Measurements Cell viability was assessed at Day 12 of cell culture by using the Cell Titer 96 (r) Aqueous One Solution Cell Proliferation Assay (Promega, Charbonnières-les-Bains, France) (n=3 cultures, 36 wells per experimental group). The assay was a colorimetric method, which was based on the use of the 3-(4,5-dimethylthiazol-2-yl)-5-(3-carboxymethoxyphenyl)-2-(4-sulfophenyl)-2H-tetrazolium inner salt (MTS), a marker of mitochondrial activity and an electron-coupling reagent (phenazine ethosulfate, PES). The MTS tetrazolium compound was bioreduced by cells into a colored formazan product that is soluble in tissue culture medium.

At Day 12, the totality of cell culture medium was removed and replaced by 500 µl of Neurobasal medium+ Cell Titer 96 Aqueous One Solution kit: Cell Titer 96 (r) Aqueous One Solution Cell Proliferation Assay Kit. According to the Proliferation Assay Kit protocol, cells were incubated for 4 hours at 37° C. in the humidified 5% CO2 atmosphere incubator. The reaction was stopped with 2% Sodium Dodecyl Sulfate (SDS). Optical density was measured 4 hours later at 490 nm utilizing a Labsystem Multiscan microplate reader (Labsystem Multiscan RC, VWR International, Fontenay sous Bois, France). Background absorbance at 620 was subtracted. Results were expressed in Optical Density (OD×10-3) representing the number of viable cells. Data was expressed as the percentage of cell viability, which was calculated by dividing the absorbance value of treated samples by that of the untreated control within each group.

Neuronal injury was quantitatively assessed by the measurement of lactic dehydrogenase (LDH) release from cultured neurons incubated in cell culture mediu at Day 12 of cell culture (Koh and Choi, 1987). The LDH release assay provided a measure of cytoplasmic membrane integrity. At Day 12, 100 µl of the cell culture medium was transferred from culture wells to 96-well plates and mixed with 100 µl of reaction solution according to LDH assay kit (Roche Diagnostic: Cytotoxicity Detection kit: ref 1644793, Indianapolis, USA). Optical density (OD) was measured 30 minutes later at 492 nm utilizing a Labsystem Multiscan microplate reader (Labsystem Multiscan RC, VWR International, Fontenay sous Bois, France). Background absorbance at 620 is subtracted. Neurons exposed to a lysis solution (PBS containing 0.1% Triton X-100) were used as positive control and set as 100% LDH release. Data was expressed as the ratio of LDH efflux/cell viability.

Results corresponded to the mean of three independent experiments with triplicate determination. Statistical analyses of cell viability and LDH results were assessed using one factor (analysis of variance) ANOVA test following by post-hoc test ($P<0.05$).

C. Focal Ischemia

The researchers, who carried out the ischemic surgery and measured infarct volumes were double-blinded in regard to the treatment code.

Model of Focal Ischmia

Focal ischemia was induced on Adult male C57/B16 mice, weighing 22 to 26 g (7-9 weeks old) by occlusion of the left middle cerebral artery (MCA) using an intraluminal filament technique (Huang et al., 1994) The left common and external carotid arteries were isolated and ligated with a silk 4-0 silk suture (Ethicon). A temporary yasargil aneurysm clip (BMH31, Aesculap, Tuttlingen, Germany) was temporarily placed on the internal carotid artery. A 6-0 coated filament (Doccol, Redlands, Calif., USA), was introduced through a small incision into the common carotid artery and 13 mm distal to the carotid bifurcation for occlusion of the origin of the MCA. Animals were kept at 37° C. for one hour, after which time, the thread was carefully withdrawn to allow reperfusion of the MCA territory. To control the MCAO severity regional CBF (rCBF) was determined by laser-Doppler flowmetry (Perimed) using a flexible 0.5-mm fiber optic extension to the masterprobe fixed on the intact skull over the ischemic cortex (2 mm posterior and 6 mm lateral from the bregma). Sham-operation was performed inserting the thread into the common carotid artery without advancing it to occlude the MCA. The animals were allowed to regain full consciousness on a heating pad before returning to the cage.

Determination of Infarct Volume

At 30 hours after reperfusion, cresyl violet staining on coronal frozen brain sections (10 μm-thick) was performed using a solution of 1% cresyl violet in 0.25% acetic acid and mounted with Entellan. The striatal and cortical areas of infarction, outlined in light were measured on each section using a computer image analysis system and corrected for brain edema according to Golanov and Reis (Golanov and Reis, 1995). Infarct volume, expressed in $mm^3$ was calculated by a linear integration of the corrected lesions areas as previously described (Heurteaux et al., 2006a).

D. Drug Treatments

The composition of NeuroAid II (MLC 901) used (0.4 g per capsule) was as follows:
    0.57 g Radix astragali,
    0.114 g Radix salvia miltiorrhizae,
    0.114 g Radix paeoniae rubra,
    0.114 g Rhizoma chuanxiong,
    0.114 g Radix angelicae sinensis,
    0.114 g Carthamus tinctorius,
    0.114 g *Prunus persica*,
    0.114 g Radix polygalae,
    0.114 g Rhizoma acori tatarinowii,
    0.0665 *Hirudo*.

For in vitro experiments, cell treatment with NeuroAid II (MLC 901), Rhizoma chuanxiong, Radix *angelicae sinensis* and combined Rhizoma chuanxiong/Radix *angelicae sinensis* were at the concentration of 1 μg/ml, starting at Day 3 of culture during 12 days (corresponding to 15 days of culture).

For in vivo post-treatment, mice were intraperitonally injected with a single dose of 2 μg/ml NeuroAid II (MLC 901) solution diluted in saline (as vehicle) in a total volume of 500 μl/mouse weighing 25 g, 3 and 24 hours following the end of ischemia. For in vivo pre-treatment, NeuroAid II (MLC 901), Rhizoma chuanxiong, Radix *angelicae sinensis* and combined Rhizoma chuanxiong/Radix *angelicae sinensis* pre-treatment was given in drinking water at the concentration of 6 mg/ml during the 6 weeks before the induction of ischemia.

E. Immunohistochemistry on Cortical Neurons in Culture

Cortical cells were fixed on coverslips with 4% paraformaldehyde/PBS, permeabilized in 0.3% polyoxyethylensorbitan monolaurate (Tween 20, Sigma) for 10 min and blocked with 2.5% donkey serum in PBS for 2 hours at room temperature. Cells were incubated with a goat anti-doublecortin (DCX) antibody (1:200, SC-8066, Santa Cruz Biotechnology Inc., Santa Cruz, Calif.) in 2% donkey serum/phosphate buffer saline overnight (Heurteaux et al., 2006b). After 3 washes in phosphate buffer saline (PBS), cells were incubated in anti-goat Alexa 488-coupled antibodies (FluoProbes, Interchim, Montlucon, France) in 2% donkey serum for 2 hours and washed three times in PBS for 5 minutes each. The neurons were then incubated in Hoechst solution (3 μl in 10 ml, Sigma-Aldrich Chimie, Saint Quentin Fallavier, France) for 10 min to label cell nuclei. After 2 washes in PBS and 1 wash in water, the coverslips were dried and mounted on glass slides with Fluoroprep (75521; Biomérieux: Marcy l'Etoile, France. Cells were observed using epifluorescence microscopy.

Signal specificity was assessed in negative control coverslips by omitting primary antibody. Epifluorescence microscopy images of protein labeling were captured with identical time of exposition after spectral correction of the autofluorescence background. The differentiated neurites of cortical neurons in culture were observed by DCX immunostaining at Day 12 of treatment. Neurite outgrowth was determined on epifluorescence microscopy by measuring total length of neurites in culture dishes at different times of treatment using a cell photo image and Neurite Tracer Image J software (Pool et al., 2008).

F. Statistical Analyses

Data was expressed as mean±S.E.M. Statistical analysis of differences between groups was performed by using unpaired t test or ANOVA. Where F ratios were significant, statistical analyses were extended and post-hoc comparisons made by using Tukey's test multiple comparison tests. In all analyses, the level of significance was set at $P<0.05$.

Example 6

Comparative Effects Between NeuroAid II (MLC 901), Rhizoma Chuanxiong, Radix Angelicae Sinensis and Combined Rhizoma Chuanxiong/Radix Angelicae Sinensis on Cell Viability and LDH Release Cortical cells, as prepared by the methods disclosed above, were exposed to a concentration of 1 µg/ml NeuroAid II (MLC 901), Rhizoma chuanxiong, Radix *angelicae sinensis* or combined Rhizoma chuanxiong/Radix *angelicae sinensis* during 12 days.

Figure 10:
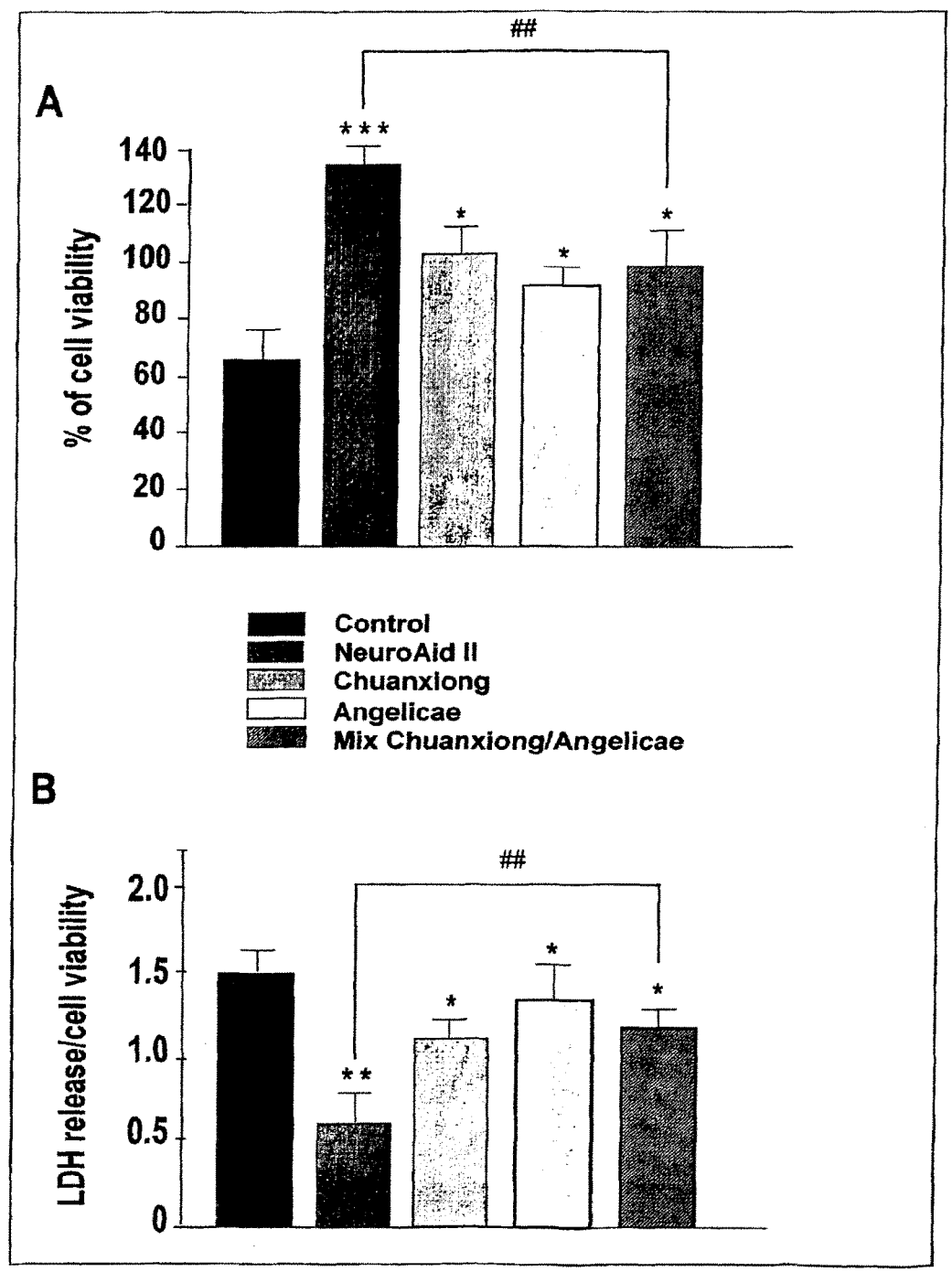
FIG. 10 shows bar charts on the comparative effects of NeuroAid II (MLC 901), Rhizoma chuanxiong Radix *angelicae sinensis* and combined Rhizoma chuanxiong/Radix *angelicae sinensis* treatments (1 µg/ml) on cortical neurons in culture estimated at Day 12 of treatment.

The effects of NeuroAid II (MLC 901) to those of Rhizoma chuanxiong, Radix *angelicae sinensis* or combined Rhizoma chuanxiong/Radix *angelicae sinensis* treatments against neurodegeneration of cortical cells were compared at Day 15 of culture (Day 12 of treatment) by using cell viability and LDH measurements as disclosed in the methods above. The results are shown in FIG. 10.

Results

FIG. 10A shows that at the concentration of 1 µg/ml, the three treatments induced a significant increase in neuronal viability as compared to control (*P<0.05, P<0.01, *P<0.001). However, NeuroAid II (MLC 901) demonstrated a higher efficacy on cell survival compared to Rhizoma chuanxiong or Radix *angelicae sinensis* treatments. As shown in FIG. 10A, a NeuroAid II (MLC 901) treatment induced an approximately 51% increase of cell viability, as compared to the control (***P<0.001), while the increase in cell survival induced by Rhizoma chuanxiong, Radix *angelicae sinensis* and combined Rhizoma chuanxiong/Radix *angelicae sinensis* was of 37%, 29.5% and 35% respectively. There was a significant difference of efficacy between NeuroAid II (MLC 901) and Rhizoma chuanxiong, Radix *angelicae sinensis* and combined Rhizoma chuanxiong/Radix *angelicae sinensis* treatments (##P<0.1) (n=36 wells per group)

It is well known that increased cell suffering that leads to cell death is associated with increased Lactate DeHydrogenase (LDH) release. FIG. 10B shows that compared to the control, the three treatments significantly reduced the ratio LDH release/cell viability after 12 days of treatment (*P<0.05 and **P<0.01). FIG. 10B also shows that NeuroAid II (MLC 901) significantly reduced LDH release when compared to Rhizoma chuanxiong, Radix *angelicae sinensis* treatment or combined Rhizoma chuanxiong/Radix *angelicae sinensis* (##P<0.01) (n=36 wells per group).

Based on the experimental data in Example 6, it can be demonstrated that NeuroAid II (MLC 901) is more potent in increasing cell viability and reducing LDH release, in culture than either Rhizoma chuanxiong, Radix *angelicae sinensis* or combined Rhizoma chuanxiong/Radix *angelicae sinensis*.

Example 7

Comparative In Vivo Effects of NeuroAid II (MLC 901), Rhizoma Chuanxiong, Radix Angelicae Sinensis and Combined Rhizoma Chuanxiong/Radix Angelicae Sinensis Against Ischemic Brain Injury In Vivo Post-Treatment:

To compare the effects of NeuroAid II (MLC 901), Rhizoma chuanxiong, Radix *angelicae sinensis* and combined Rhizoma chuanxiong/Radix *angelicae sinensis* in vivo, each treatment was tested in a mouse model of focal ischemia.

Ischemia was induced by transient middle cerebral artery occlusion (MCAO) for 60 min (Huang et al., 1994). Mice (n=12) were subjected to focal ischemia and intraperitoneally injected at 3 hours and then again at 24 hours after MCAO with a single dose of 1 µg of NeuroAid II (MLC 901), Rhizoma chuanxiong, Radix *angelicae sinensis* or combined Rhizoma chuanxiong/Radix *angelicae sinensis* solution.

Figure 11:
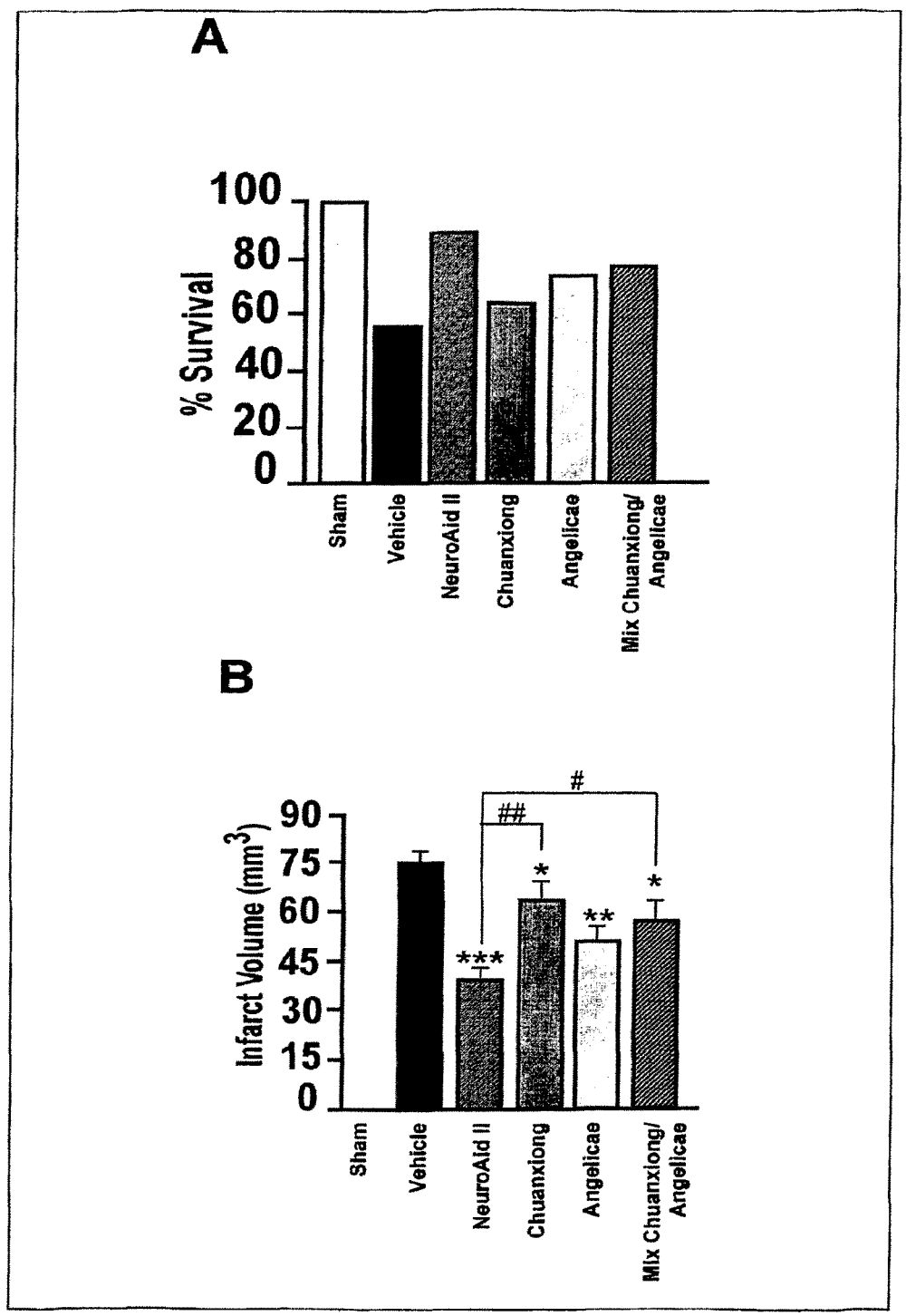
FIG. 11 shows bar charts on the comparative effects of a post-treatment with NeuroAid II (MLC 901), Rhizoma chuanxiong, Radix *angelicae sinensis* and combined Rhizoma chuanxiong/Radix *angelicae sinensis* against ischemic brain injury in vivo.

Acute administration of each treatment induced a significant survival rate, with a better efficiency obtained with NeuroAid II (MLC 901). FIG. 11A shows that a survival rate of 89% was achieved with NeuroAid II (MLC 901) as compared to a survival rate of 58.5%, 64%, 73% and 75% in ischemic vehicle-, rhizoma chuanxiong-, radix angelicae-treated and combined Rhizoma chuanxiong/Radix *angelicae sinensis* mice, respectively.

The drastic decrease of cerebral infarction as shown in FIG. 11B confirms that the best result was observed with NeuroAid II (MLC 901). FIG. 11B shows that NeuroAid II (MLC 901) reduced the stroke volume by 48.4% (***P<0.001) as compared to control ischemic mice at 30 h post-ischemia. The infarct size in *rhizoma chuanxiong*-, radix angelicae-treated and combined Rhizoma chuanxiong/Radix *angelicae sinensis* mice was significantly larger than in NeuroAid II (MLC 901)-treated animals after 30 hours of reperfusion (FIG. 11B, #P<0.05, ##P<0.001 versus NeuroAid II (MLC 901) group).

Pre-Treatment:

To compare the potential in vivo effects between MLC 901, Rhizoma chuanxiong and Radix *angelicae sinensis* in prevention against stroke, each treatment was tested in pre-treatment.

Figure 12:
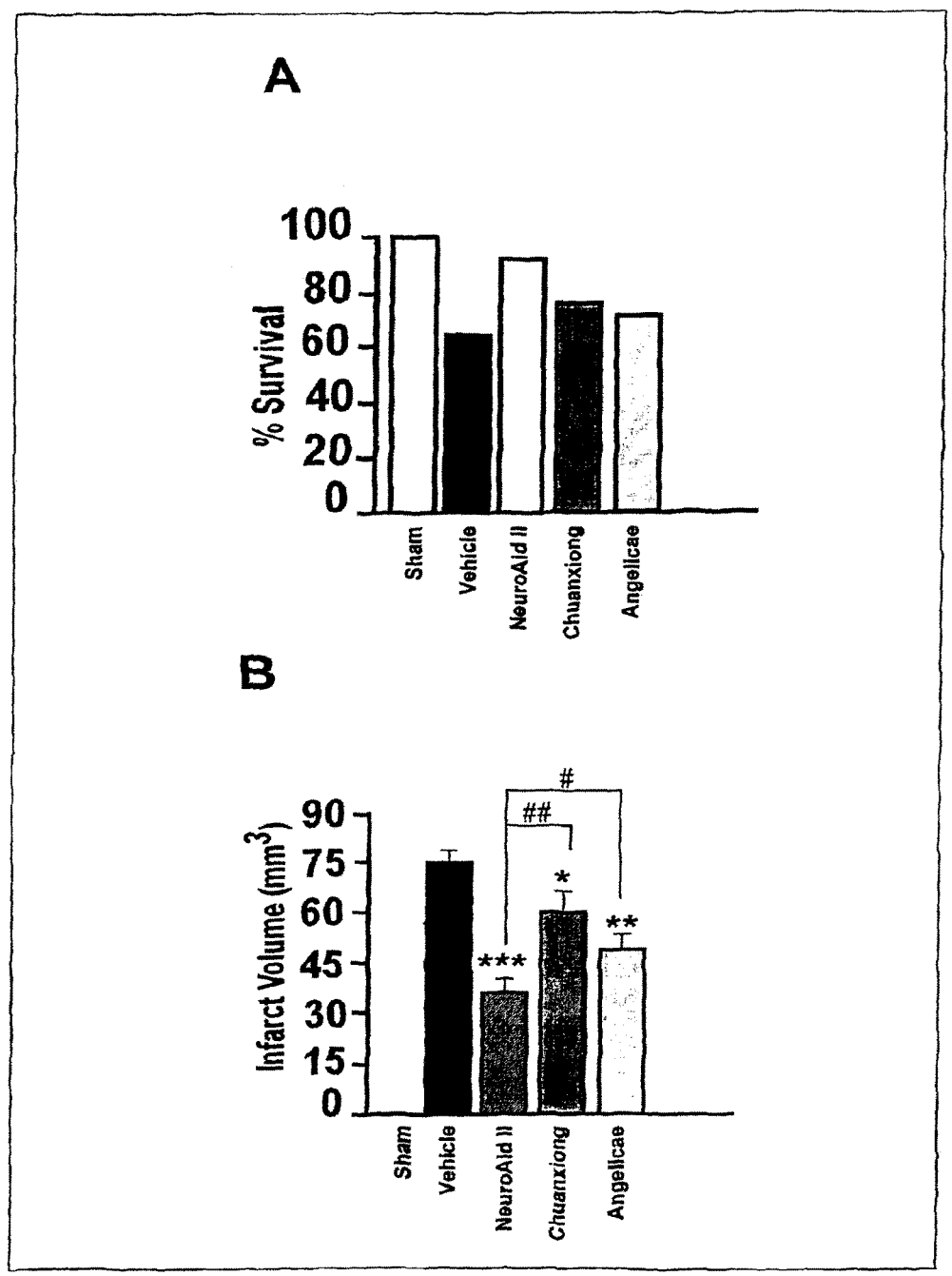
FIG. 12 shows bar charts on the comparative effects of a pre-treatment with NeuroAid II (MLC 901), Rhizoma chuanxiong and Radix *angelicae sinensis* against ischemic brain injury in vivo.

The animals (n=12) were treated with NeuroAid II (MLC 901), Rhizoma chuanxiong or Radix *angelicae sinensis* administered in the drinking water (6 mg/ml) for 6 weeks before the induction of ischemia. There was no significant difference in the consumption of food and drinking solution between vehicle and NeuroAid II (MLC 901) treated groups. FIG. 12A shows that a 6 week pretreatment of NeuroAid II (MLC 901), Rhizoma chuanxiong and Radix *angelicae sinensis* induced a reduction of the mortality of treated animals, compared to the control ischemic mice.

Pre-treatment induced a survival rate of 92%, 78% and 70% in NeuroAid II (MLC 901), Rhizoma chuanxiong and Radix angelicae *sinensis*, respectively when compared to 62.5% in the control group. The best result for diminishing the effects of stroke or neurodegeneration in predisposed subjects or subjects at the risk of stroke or neurodegeneration obtained with. NeuroAid II (MLC 901) was confirmed by a significant decrease of the infarct volume, which was 39% and 24.5% less important as compared to Rhizoma chuanxiong and Radix angelicae *sinensis* (FIG. 3B, P<0.01).

These studies in Example 7 demonstrate that NeuroAid II (MLC 901) is more potent than either Rhizoma chuanxiong or Radix *angelicae sinensis* in pre-treatment of focal ischemia and NeuroAid II (MLC 901) is more potent than either Rhizoma chuanxiong, Radix *angelicae sinensis* or combined Rhizoma chuanxiong/Radix *angelicae sinensis* in post-treatment of focal ischemia.

Example 8

Comparative Effects of NeuroAid II (MLC 901), Rhizoma Chuanxiong, Radix Angelicae Sinensis and Combined Rhizoma Chuanxiong/Radix Angelicae Sinensis on Neuroproliferation and Neurite Outgrowth To analyze the effects of NeuroAid II (MLC 901), Rhizoma chuanxiong, Radix *angelicae sinensis* and combined Rhizoma chuanxiong/Radix *angelicae sinensis* on neuronal proliferation and neurite outgrowth, the expression of DCX in cultured cortical cells from embryonic mice was compared after 14 days of treatment.

Figure 13:
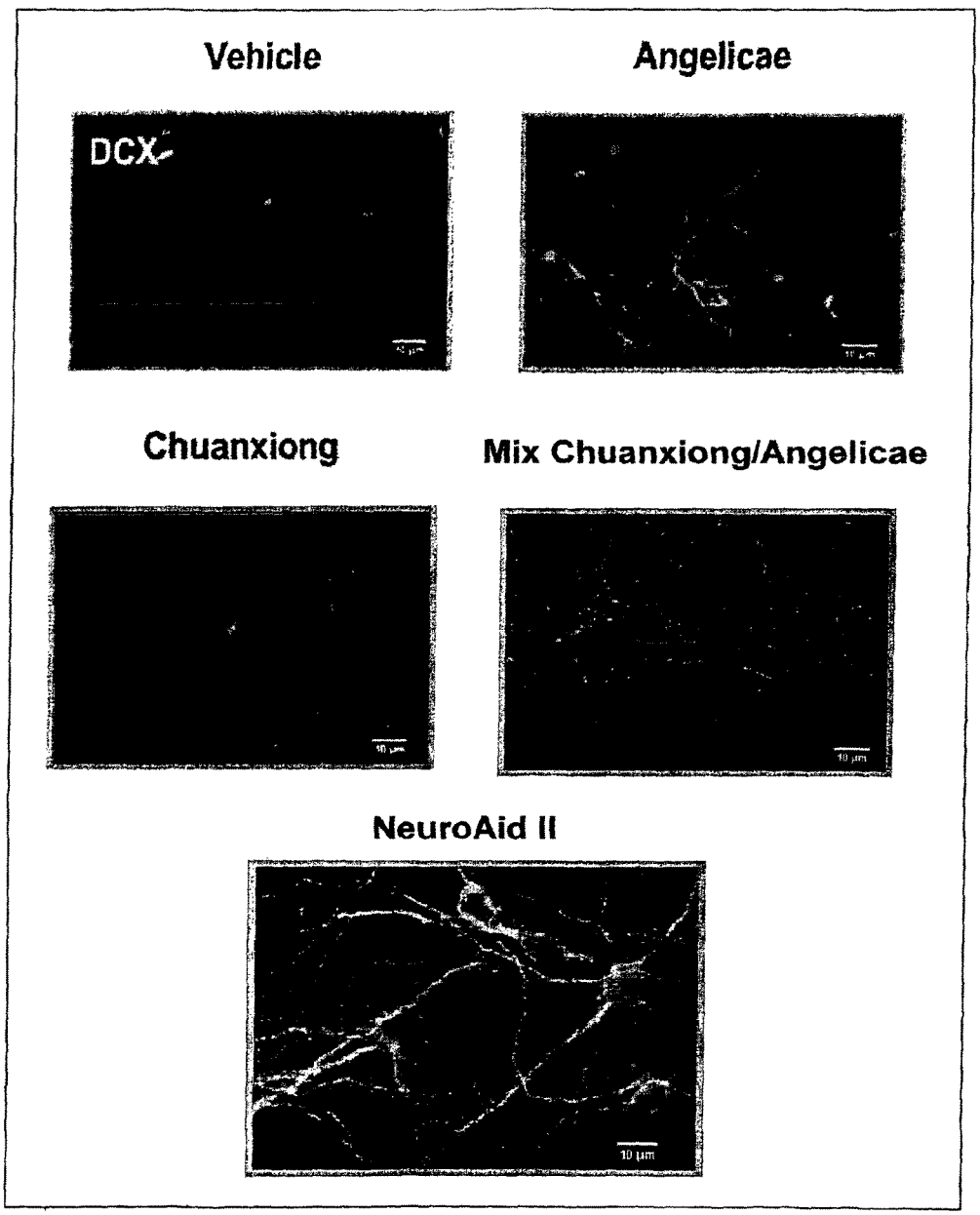
FIG. 13 shows representative epifluorecence microscopy photographs of the comparative effects between NeuroAid II (MLC 901), Rhizoma chuanxiong, Radix *angelicae sinensis* and combined Rhizoma chuanxiong/Radix *angelicae sinensis* treatment (1 µg/ml) on in vitro DCX immunoexpression in cultured cortical cells at Day 12 of treatment.

Representative epifluorescence microscopy images of DCX staining are shown in FIG. 13. FIG. 13 shows that there was an increase of DCX expression induced by NeuroAid II (MLC 901), Radix *angelicae sinensis* treatment or combined Rhizoma chuanxiong/Radix *angelicae sinensis*, highlighting the development of an important axonal and dendritic network with these three treatments as compared to cells treated with the vehicle group or Rhizoma chuanxiong alone.

Figure 14:
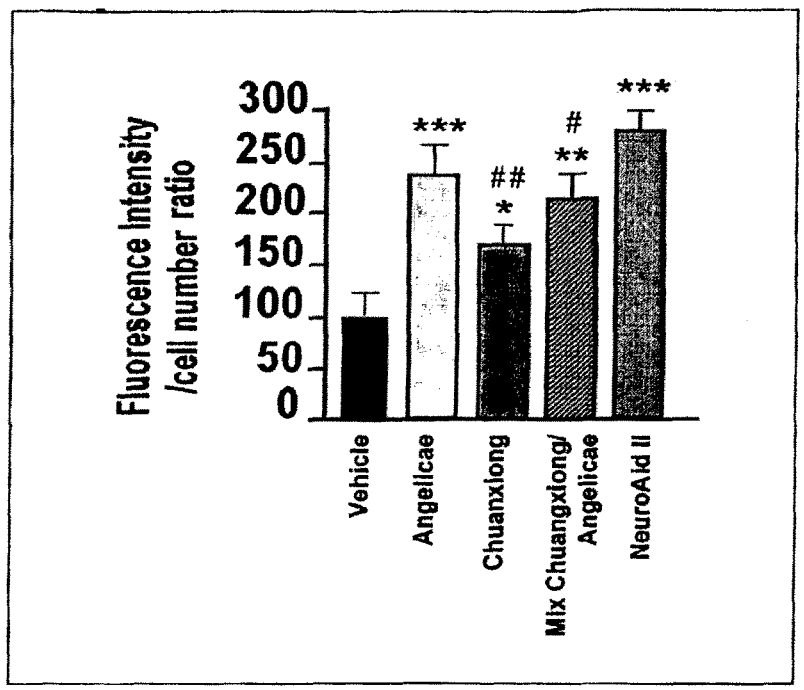
FIG. 14 shows bar charts of DCX signal intensity in immunostained neurons observed in epifluorecence microscopy.

Quantification of the fluorescence intensity in each epifluorescence microscopy image was shown in FIG. 14. FIG. 14 showed that the best neuroproliferative effect was obtained in cortical cultures treated with NeuroAid II (MLC 901).

To investigate whether NeuroAid II (MLC 901), Rhizoma chuanxiong, Radix *angelicae sinensis* or combined Rhizoma chuanxiong/Radix *angelicae sinensis* treatment could promote neurite outgrowth, the total length of neurites in cultured cortical neurons was measured at Day 14 of treatment.

Figure 15:
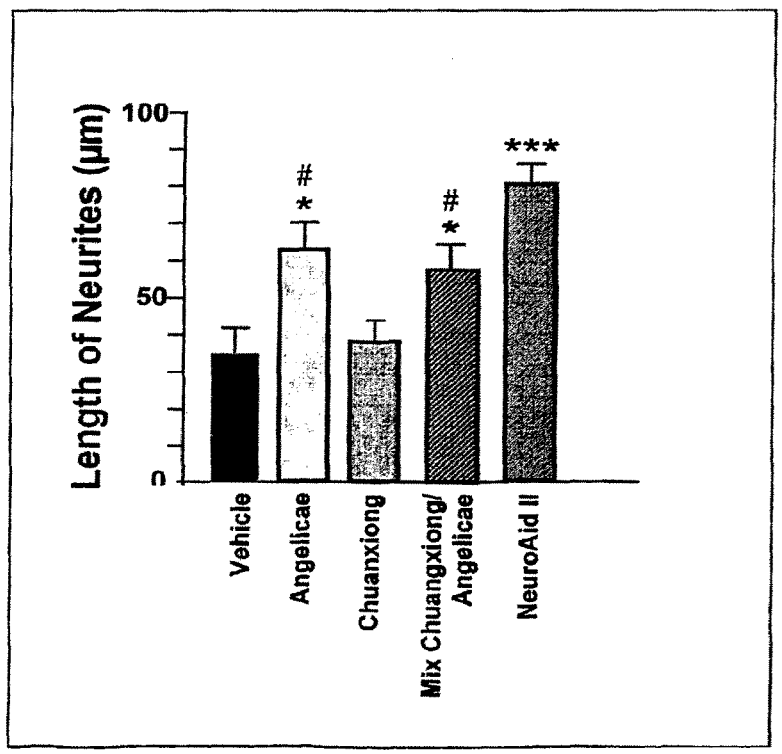
FIG. 15 shows bar charts of the neurite outgrowth obtained by measuring on epifluorecence microscopy, the total length of neurite (μm) in function of treatments.

FIG. 15 shows that NeuroAid II (MLC 901), Radix *angelicae sinensis* and combined Rhizoma chuanxiong/Radix *angelicae sinensis* induced a significant neurite outgrowth when compared to vehicle group (*P<0.05, ***P<0.001). The best neurite outgrowth promoting activity was observed for NeuroAid II (MLC 901) when compared to that of Radix *angelicae sinensis* alone or combined Rhizoma chuanxiong/Radix *angelicae sinensis* (#P<0.05).

These studies in Example 8 demonstrate that NeuroAid II (MLC 901) is more potent than either Rhizoma chuanxiong, Radix *angelicae sinensis* or combined Rhizoma chuanxiong/Radix *angelicae sinensis* for producing neuroproliferation and neurite outgrowth.

Applications

Advantageously, the disclosed compositions and methods provide a new therapeutic strategy, which focuses on neural repair and restoring neurological functions.

The disclosed methods provide regenerative therapies for treating nervous system injuries and neurological diseases, by promoting neural growth so as to enable damaged or diseased nerves to function again.

The disclosed methods can also be used to promote in vitro cell growth. Advantageously, the in vitro culture of various cells may be used for tissue engineering or ex vivo therapeutic uses.

It will be apparent that various other modifications and adaptations of the invention will be apparent to the person skilled in the art after reading the foregoing disclosure without departing from the spirit and scope of the invention and it is intended that all such modifications and adaptations come within the scope of the appended claims.

The invention claimed is:

1. A composition for diminishing the effects of a stroke and/or a neurodegenerative disorder comprising effective amounts of Radix Angelicae (root of Chinese Angelica or Danq Gui), Rhizome of *Ligusticum* Chuanxionq (Chuan Xiong), Radix Polygalae (root of thinleaf milkwort, *Polygala tenuifolia* Willd., *Polygala sibirica* L. or Yuanzhi), and Radix *Astragali* (root of Membranous Milkvetch or Huang Qi), wherein the Radix Angelicae, Rhizome of *Ligusticum* Chuanxionq, Radix Polygalae, and Radix Astragali are present in the composition in a ratio of about 1:1:1:5 by weight, respectively.

2. The composition of claim 1, wherein the composition further comprises any one or more of the following components: Radix et Rhizoma Salviae Miltiorrhizae (Red Sage root or Dan Shen), Radix Paeoniae Rubra (Red Peony root, *Paeonia lactiflora* Pall, *Paeonia veitchii* Lynch or Chi Shao), Flower of *Carthamus Tinctorius* (Safflower or HongHua), *Prunus Persica* (Peach seed or Taoren), and Rhizoma acori Tatarinowii (rhizome of grassleaf sweetflag or Shichangpu).

3. The composition according to claim 2, wherein the composition further comprises Radix et Rhizoma Salviae Miltiorrhizae (Red Sage root or Dan Shen), Radix Paeoniae Rubra (Red Peony root, *Paeonia lactiflora* Pall, *Paeonia veitchii* Lynch or Chi Shao), Flower of *Carthamus Tinctorius* (Safflower or HongHua), *Prunus Persica* (Peach seed or Taoren), and Rhizoma acori Tatarinowii (rhizome of grassleaf sweetflag or Shichangpu).

4. The composition according to claim 1, wherein the composition further comprises an agent used in Western medicine for diminishing the effects of stroke or neurodegeneration.

5. A composition for diminishing the effects of a stroke and/or a neurodegenerative disorder comprising effective amounts of consisting essentially of Radix Angelicae (root of Chinese Angelica or Dang Gui), Rhizome of *Ligusticum* Chuanxiong (Chuan Xiong), Radix Polygalae (root of thinleaf milkwort, *Polygala tenuifolia* Willd., *Polygala sibirica* L. or Yuanzhi), and Radix Astragali (root of Membranous Milkvetch or Huang Qi), wherein the Radix Angelicae, Rhizome of *Ligusticum* Chuanxiong, Radix Polygalae, and Radix Astragali are present in the composition in a ratio of about 1:1:1:5 by weight, respectively.

6. A composition for diminishing the effects of a stroke and/or a neurodegenerative disorder comprising effective amounts of consisting essentially of Radix Angelicae (root of Chinese Angelica or Dang Gui), Rhizome of *Ligusticum* Chuanxiong (Chuan Xiong), Radix Polygalae (root of thinleaf milkwort, *Polygala tenuifolia* Willd., *Polygala sibirica* L. or Yuanzhi), and Radix Astragali (root of Membranous Milkvetch or Huang Qi), and an agent used in Western medicine for diminishing the effects of stroke or neurodegeneration, wherein the Radix Angelicae, Rhizome of *Ligusticum* Chuanxiong, Radix Polygalae, and Radix Astragali are present in the composition in a ratio of about 1:1:1:5 by weight, respectively.

\* \* \* \* \*

UNITED STATES PATENT AND TRADEMARK OFFICE
CERTIFICATE OF CORRECTION

PATENT NO.         : 10,188,688 B2
APPLICATION NO.    : 15/018505
DATED              : January 29, 2019
INVENTOR(S)        : Michel Maurice Jacques Lazdunski et al.

It is certified that error appears in the above-identified patent and that said Letters Patent is hereby corrected as shown below:

In the Claims

At Column 26, Lines 38-40, "A composition for diminishing the effects of a stroke and/or a neurodegenerative disorder comprising effective amounts of consisting essentially of Radix Angelicae" should be -- A composition for diminishing the effects of a stroke and/or a neurodegenerative disorder consisting essentially of effective amounts of Radix Angelicae --.

At Column 26, Lines 49-51, "A composition for diminishing the effects of a stroke and/or a neurodegenerative disorder comprising effective amounts of consisting essentially of Radix Angelicae" should be -- A composition for diminishing the effects of a stroke and/or a neurodegenerative disorder consisting essentially of effective amounts of Radix Angelicae --.

Signed and Sealed this
Second Day of April, 2019

Andrei Iancu
*Director of the United States Patent and Trademark Office*